US009994541B2

(12) United States Patent
Batthyány et al.

(10) Patent No.: US 9,994,541 B2
(45) Date of Patent: Jun. 12, 2018

(54) NITROALKENE TROLOX DERIVATIVES AND METHODS OF USE THEREOF IN THE TREATMENT AND PREVENTION OF INFLAMMATION RELATED CONDITIONS

(71) Applicant: Institut Pasteur de Montevideo, Montevideo (UY)

(72) Inventors: Carlos Batthyány, Montevideo (UY); Gloria Virginia López, Montevideo (UY); Rosina Dapueto, Montevideo (UY); Carlos Escande, Montevideo (UY); Jorge Rodriguez Duarte, Ciudad de la Costa (UY)

( * ) Notice: Subject to any disclaimer, the term of this patent is extended or adjusted under 35 U.S.C. 154(b) by 0 days. days.

(21) Appl. No.: 15/244,370

(22) Filed: Aug. 23, 2016

(65) Prior Publication Data
US 2018/0057475 A1 Mar. 1, 2018

(51) Int. Cl.
*C07D 311/58* (2006.01)
(52) U.S. Cl.
CPC ................. *C07D 311/58* (2013.01)
(58) Field of Classification Search
None
See application file for complete search history.

(56) References Cited

FOREIGN PATENT DOCUMENTS

WO    2015072327  A1   5/2015
WO    WO 2015/073527   *   5/2015  ........... C07D 311/74

OTHER PUBLICATIONS

Abraham, N. G., and Kappas, A., "Heme oxygenase and the cardiovascular-renal system," Free Radic Biol Med 39:1-25, Elsevier Inc. (2005).
Baker P.R., Schopfer F.J., O'Donnell V.B., Freeman B.A., "Convergence of nitric oxide and lipid signaling: anti-inflammatory nitro-fatty acids," Free Radic Biol Med 46:989-1003, Elsevier Inc. (2009).
Batthyány, C., Schopfer, F.J., Baker, P.R.S., Durán, R., Baker, L.M.S., Huang, Y., Cerveñansky, C., Branchaud, B.P., and Freeman, B.A., "Reversible Post-translational Modification of Proteins by Nitrated Fatty Acids in Vivo," J Biol Chem, American Society for Biochemistry and Molecular Biology 281:20450-20453 (2006).
Bonacci, G., Baker, P.R.S., Salvatore, S.R., Shores, D., Khoo, N.K.H., Koenitzer, J.R., Dario, A.V., Woodcock, S.A., Golin-Bisello, F., Cole, M.P., Watkins, S., St. Criox, C., Batthyány, C.I., Freeman, B.A., and Schopfer, F.J., "Conjugated Linoleic Acid Is a Preferential Substrate for Fatty Acid Nitration," J Biol Chem 287:44071-44082, American Society for Biochemistry and Molecular Biology (2012).
Bonacci, G., Schopfer, F.J., Batthyány, C.I., Rudolph, T.K., Rudolph, V., Khoo, N.K.H., Kelley, E.E., Freeman, B.A., "Electrophilic Fatty Acids Regulate Matrix Metalloproteinase Activity and Expression," J Biol Chem 286(18): 16074-16081, American Society for Biochemistry and Molecular Biology (2011).
Bouhlel M.A., Derudas B., Rigamonti E., Dievart R., Brozek J., Haulon S., Zawadzki C., Jude B., Torpier G., Marx N., Staels B., Chinetti-Gbaguidi G.," PPARgamma Activation Primes Human Monocytes into Alternative M2 Macrophages with Anti-Inflammatory Properties," Cell Metab 6:137-143, Elsevier Inc. (2007).
Cock T.A., Houten S.M., Auwerx J., "Peroxisome proliferator-activated receptor-gamma: too much of a good thing causes harm," EMBO Rep 5(2):142-147, European Molecular Biology Organization (2004).
Cole, M.P., Rudolph, T.K., Khoo, N.K.H., Motanya, U.N., Golin-Bisello, F., Wertz, J.W., Schopfer, F.J., Rudolph, V., Woodcock, S.A., Bolisetty, S., Ali, M.S., Zhang, J., Chen, Y.E., Agarwal, A., Freeman, B.A., and Bauer, P.M., "Nitro-Fatty Acid Inhibition of Neointima Formation After Endothelial Vessel Injury," Cir Res 105:965-972, American Heart Association, Inc. (2009).
Elbrecht A., Chen Y., Adams A., Berger J., Griffin P., Klatt T., Zhang B., Menke J., Zhou G., Smith R.G., Moller D.E. "L-764406 is a Partial Agonist of Human Peroxisome Proliferator-activated Receptor gamma. The Role of Cys313 in Ligand Binding," J Biol Chem 274(12):7913-7922, American Society for Biochemistry and Molecular Biology (1999).
Holtzclaw, W. D., Dinkova-Kostova, A. T., and Talalay, P., "Protection against electrophile and oxidative stress by induction of phase 2 genes: the quest for the elusive sensor that responds to inducers," Adv Enzyme Regul 44: 335-367, Elsevier Ltd. (2004).
Kansanen, E., Jyrkkanen, H. K. Volger, O. L., Leinonen, H., Kivela, A. M., Hakkinen, S.K., Woodcock, S. R., Schopfer, F. J., Horrevoets, A. J., Yla-Herttuala, S., Freeman, B. A., and Levonen, A. L., "Nrf2-dependent and-independent Responses to Nitro-fatty Acids in Human Endothelial Cells: Identification of Heat Shock Response as the Major Pathway Activated by Nitro-Oleic Acid," J Biol Chem 284(48): 33233-33241, American Society for Biochemistry and Molecular Biology (2009).
Kansanen, E., Bonacci, G., Schopfer, F. J., Kuosmanen, S. M., Tong, K. I., Leinonen, H., Woodcock, S. R., Yamamoto, M., Carlberg, C., Yla-Herttuala, S., Freeman, B. A., and Levonen, A. L., "Electrophilic Nitro-Fatty Acids Activate NRF2 by a KEAP1 Cysteine 151-independent Mechanism," J Biol Chem 286(16):14019-14027, American Society for Biochemistry and Molecular Biology (2011).
Kelley, E.E., Baust, J., Bonacci, G., Golin-Bisello, F., Devlin, J.E., St. Criox, C., Watkins, S., Gor, S., Nadiezhda, C.M., Weidert, E.R., Frisbee, J.C., Gladwin, M.T., Champion, H.C.., Freeman, B.A., Khoo, N.K.H., "Fatty acid nitroalkenes ameliorate glucose intolerance and pulmonary hypertension in high-fat diet-induced obesity," Cardivascular Res 101 (3): 352-363, European Society of Cardiology (2014).
Khoo, N.K.H. and Freeman, B.A., "Electrophilic Nitro-Fatty Acids: Anti-inflammatory Mediators in the Vascular Compartment," Cuff Opin Pharmacol 10(2): 179-184, Elsevier Science Ltd., (2010).

(Continued)

*Primary Examiner* — Craig D Ricci
(74) *Attorney, Agent, or Firm* — Cozen O'Connor

(57) ABSTRACT

The present invention is directed to a class of anti-inflammatory, antioxidant nitroalkene compounds used in biological or biochemical applications to reduce oxidative stress or damage. The nitroalkene compounds described herein further avoid disadvantageous metabolism currently present in this field.

14 Claims, 12 Drawing Sheets

(56) References Cited

OTHER PUBLICATIONS

Lei H. and Atkinson, J., "Synthesis of Phytyl- and Chroman-Derivatized Photoaffinity Labels Based on alpha-Tocopherol," J Org Chem 2000(65):2560-2567, American Chemical Society (2007).

Levonen, A. L., Inkala, M., Heikura, T., Jauhiainen, S., Jyrkkanen, H. K., Kansanen, E., Maatta, K., Romppanen, E., Turunen, P., Rutanen, J., and Yla-Herttuala, S., "Nrf2 Gene Transfer Induces Antioxidant Enzymes and Suppresses Smooth Muscle Cell Growth In Vitro and Reduces Oxidative Stress in Rabbit Aorta In Vivo," Arterioscler Thromb Vasc Biol 27, 741-747, American Heart Association, Inc. (2007).

Li, Y., Zhang, J., Schopfer, F.J., Martynowski, D., Garcia-Barrio, M.T., Kovach, A., Suino-Powell, K., Baker, P.R.S., Freeman, B.A., Chen, Y.E., and Xu, H.E., "Molecular recognition of nitrated fatty acids by PPAR-gamma," Nat Struct Mol Biol 15(8):865-867, Nature Publishing Group (2008).

Liu, H., Jia, H., Soovilai, S., Guan, G., Wang, M-H., Dong, Z., Symons, J.D., and Yang, T., "Nitro-oleic acid protects the mouse kidney from ischemia and reperfusion injury," Am J Physiol Renal Physiol 295:F942-F949, American Physiological Society (2008).

Motohashi, H., and Yamamoto, M., "Nrf2-Keap1 defines a physiologically important stress response mechanism," Trends Mol Med 10(11):549-557, Elsevier Ltd. (2004).

Rudolph V., Schopfer F.J., Khoo N.K., Rudolph T.K,. Cole M.P., Woodcock S.R., Bonacci G., Groeger A.L,. Golin-Bisello F., Chen C.S., Baker P.R. Freeman B.A., "Nitro-fatty Acid Metabolome: Saturation, Desaturation, beta-Oxidation, and Protein Adduction," J Biol Chem 284: 1461-1473, American Society for Biochemistry and Molecular Biology (2009).

Rudolph, T.K., Rudolph, V., Edreira, M.M., Cole, M.P., Bonacci, G., Schopfer, F.J., Woodcock, S.R., Franek, A., Pekarova, M., Khoo, N.K.H., Hasty, A.H., Baldus, S., and Freeman, B.A., "Nitro-Fatty Acids Reduce Atherosclerosis in Apolipoprotein E-Deficient Mice," Anterioscler Thromb Vasc Biol 30:938-945, American Heart Association, Inc. (2010).

Saikia, A.K., Barua, N.C., Sharma, R.P., Ghosh, A. C., "An Improved Synthesis of Conjugated Nitroolefins," SYN Short Papers 7:685-686, Thieme Verlagsgruppe (1994).

Schopfer F.J., Batthyány C.I.,Baker, P.R.S., Bonacci, G., Cole, M.P., Rudolph, V., Groeger, A.L., Rudolph, T.K., Nadtochiy, S., Brookes, P.S., Freeman, B.A., "Detection and quantification of protein adduction by electrophilic fatty acids: mitochondrial generation of fatty acid nitroalkene derivatives," Free Rad Biol Med 46:1250-1259, Elsevier Inc. (2008).

Schopfer F.J., Cole, M.P., Groeger A.L., ChenC.-S., Khoo, N.K.H., Woodcock, S.R., Golin-Bisello, F., Motanya, U.N., Li, Y., Zhang, J., Garcia-Barrio, M.T., Rudolph, T.K., Rudolph, V., Bonacci, G., Baker, P.R.S., Xu, E.S., Batthyány C.I., Chen, E.Y., Hallis, T.M., and Freeman, B.A., "Covalent Peroxisome Proliferator-activated Receptor Adduction by Nitro-fatty Acids—Selective Ligand Activity and Anti-Diabetic Signaling Actions," J Biol Chem 285 (16):12321-12333, American Society for Biochemistry and Molecular Biology (2010).

Shiraki T., Kamiya N., Shiki S., Kodama T.S., Kakizuka A., Jingami H., "Alpha,beta-unsaturated ketone is a core moiety of natural ligands for covalent binding to peroxisome proliferator-activated receptor gamma," J Biol Chem 280: 14145-14153, American Society for Biochemistry and Molecular Biology (2005).

Talalay, P., Dinkova-Kostova, A. T., and Holtzclaw, W. D., "Importance of phase 2 gene regulation in protection against electrophile and reactive oxygen toxicity and carcinogenesis," Adv Enzyme Regul 43:121-134 (2003) Elsevier Science Ltd.

Wakabayashi, N., Dinkova-Kostova, A. T., Holtzclaw, W. D., Kang, M. I., Kobayashi, A., Yamamoto, M., Kensler, T. W., and Talalay, P., "Protection against electrophile and oxidant stress by induction of the phase 2 response: fate of cysteines of the Keap1 sensor modified by inducers," Proc Natl Acad Sci USA 101: 2040-2045, National Academy of Sciences (2004).

Yu K., Bayona W., Kallen C.B., Harding H.P., Ravera C.P., McMahon G., Brown M., Lazar M.A., "Differential Activation of Peroxisome Proliferator-Activated Receptors by Eicosanoids," J Biol Chem 270(41): 23975-23983, American Society for Biochemistry and Molecular Biology (1995).

Zhang, J., Villacorta, L., Chang, L., Zhenzhen, F., Hamblin, M., Zhu, T., Chen, S.C., Cole, M.P., Schopfer F.J., Deng, C.X., Garcia-Barrio, M.T., Feng, Y-H., Freeman, B.A., and Chen, Y.E., "Nitro-Oleic Acid Inhibits Angiotensin II-Induced Hypertension," Cir Res 107:540-248, American Heart Association, Inc. (2010).

Lopez, G.V., et al., "Second generation of alpha-tocopherol analogs-nitric oxide donors:Synthesis, physicochemical, and biological characterization," Bioorgnic & Medicinal Chemistry 15 (18): 6262-6272, Elsevier Ltd., United States, Sep. 2007.

\* cited by examiner

NITROALKENE TROLOX DERIVATIVES AND METHODS OF USE THEREOF IN THE TREATMENT AND PREVENTION OF INFLAMMATION RELATED CONDITIONS

BACKGROUND

The scope of the present invention includes compounds and pharmaceutical compositions useful as anti-inflammatory agents.

Studies have shown that endogenous electrophilic unsaturated-nitrated fatty acids, including nitro-linoleic acid ($LNO_2$) and nitro-oleic acid ($OA-NO_2$), can mediate anti-inflammatory and pro-survival signaling reactions [1]. The basis for the mediation are mainly produced because the presence of the nitro group on the double bond turns the β-carbon adjacent to the nitroalkene strongly electrophilic and reacts covalently with nucleophiles both in proteins (thiols and histidine residues) and low molecular weight molecules via Michael addition reactions [2].

Thus, biological electrophiles have emerged as mediators protecting against xenobiotic and oxidant injury. The transcription factor Nrf2 (nuclear factor erythroid 2-related factor 2)/Keap1 (Kelch-like ECH-associating protein) pathway mediates phase 2 gene activation [3]. Under normal conditions, Nrf2 localizes to the cytoplasmic suppressor protein Keap1 which has several critical cysteine residues that serve as sensors to environmental stresses such as ROS and electrophiles [3, 4]. Keap1 cysteines are oxidized or alkylated, causing a conformational change and liberating Nrf2 to translocate to the nucleus, bind to the cis-acting DNA regulatory antioxidant response element (ARE) and thereby transactivating Nrf2-dependent gene transcription [3, 4]. This includes enzymes involved in glutathione (GSH) metabolism, such as the subunits of the rate-limiting enzyme of glutathione synthesis, glutamate-cysteine ligase catalytic (GCLC) and modifier (GCLM) subunit genes. Also NAD(P)H:quinone oxidoreductase-1 (NQO1), which not only detoxifies xenobiotic quinones, but also reduces antioxidants vitamin E and coenzyme Q10 to their active form, is a Nrf2 target gene.

Additionally, HO-1 has been shown to be positively regulated by Nrf2 [5, 6]. This widespread mechanism protects against metabolic and inflammatory stress [5, 7, 8]. It is interesting to note that electrophilic nitro-fatty acids activate NRF2 by a KEAP1 cysteine 151-independent mechanism [9]. Actually, nitrated oleic acid, one of the endogenous nitroalkenes, is a Cys(151)-independent Nrf2 activator, which in turn can influence the pattern of gene expression and therapeutic actions of nitroalkenes [9].

Heme Oxygenase-1 (HO-1) also plays a central role in vascular inflammatory signaling and mediates a protective response to inflammatory stresses such as atherosclerosis, vascular restenosis and kidney diseases including transplant rejection [10]. Heme oxygenase 1 catalyzes the degradation of heme to biliverdin, iron, and carbon monoxide (CO). CO has been shown to display diverse, adaptive biological properties, including anti-inflammatory, anti-apoptotic, and vasodilatory actions [11].

Nitrated fatty acids have also been shown to be activators of peroxisome proliferator-activated receptor gamma (PPARγ). PPARγ is established as a master regulator of metabolism, inflammation, adipogenesis, and insulin sensitization [12]. High, non-physiological concentrations of native fatty acids (N50 μM), prostaglandin metabolites, and oxidized fatty acid derivatives are able to activate PPARγ, α, and δ [13,14]. Fatty acids containing an α-β-unsaturated ketone as a core structural element, such as 15d-$PGJ_2$, also activate PPARγ [15]. Docking of 15d-$PGJ_2$ to the ligand binding domain (LBD) shows that it is not sufficient to activate the receptor; rather, a covalent Michael addition reaction (locking reaction) is required for activation [13]. The PPARγ receptor contains a critical thiol (Cys285) in the LBD, with covalent modification of this highly conserved Cys285 by thiol-reactive compounds sufficient to induce partial receptor activation [16]. $NO_2$-FAs and keto-fatty acid derivatives have high binding affinities for PPAR isotypes, being PPARγ the most robustly-activated receptor [13,17]. The mechanism by which LNO2 activates PPARγ has been determined with recent solution of the crystal structure of PPARγ having LNO2 occupancy in the LBD [18,19]. Differential conformational changes to PPARγ resulting from this unique endogenous ligand have the capacity to impart unique specificity to the downstream signaling events resulting from PPARγ activation [13,19]. Interestingly, PPARγ activation skews human monocytes toward an anti-inflammatory M2 phenotype [20], another possible mechanism to further explain the anti-inflammatory, anti-atherogenic properties of endogenous nitroalkenes.

However, in vivo studies of nitrated fatty acids such as nitrated oleic acid (18:1-$NO_2$) metabolism showed that nitrated oleic acid undergoes a rapid and substantial modification that affects subsequent chemical reactivity and signaling actions [21]. More specifically, the results of the study showed the 18:1-$NO_2$ suffers rapid but reversible adduction to plasma thiols and GSH. Furthermore, a significant proportion of 18:1-$NO_2$ and its metabolites are converted to nitroalkane derivatives by saturation of the double bond, and to a lesser extent are desaturated to diene derivatives. The rapid saturation of the double bond decreases the electrophilic character of the molecule and may consequently affect the potency [22].

The study also showed that the hydrophobic nitro-oleic acid is metabolized by the β-oxidation pathways. As a result, the β-oxidized metabolite will be less hydrophobic and this will not only influence partitioning between hydrophobic and hydrophilic compartments and consequent tissue distribution, but can also affect chemical reactivity and pharmacological profiles by altering the specificity of the nitroalkenes to the biologically relevant targets.

Non-endogenous hydrophobic nitroalkene tocopherols and analogs thereof, as shown in WO 2015/073527, exhibit comparable potency as anti-inflammatory nitrated fatty acids and mimics transport processes of other lipid molecules in vivo and is closely related to lipoprotein homeostasis and metabolism which control intestinal absorption, traffic through the vascular compartment, and cellular uptake [20]. However, poor hydrosolubility of the nitroalkene tocopherol presents difficulties for traditional routes of drug delivery. Consequently, as discussed, in vivo distribution is premised on simulating the transport mechanism of endogenous lipid molecules.

A new family of nitroalkenes trolox (the hydrosoluble form of alpha-tocopherol) derivatives, provides advantages of controlling hydrosolubility, in doing so the scope of the invention includes hydrosoluble nitroalkene trolox derivatives to very hydrophobic ones. This allows the new generation of nitroalkenes to be modified for different inflammation related conditions.

SUMMARY

Within the scope of the present invention a new class of non-endogenous nitroalkene derivatives of 6-hydroxy-2,5, 7,8-tetramethylchroman-2-carboxylic acid (Trolox) which are water soluble. The water soluble non-endogenous nitroalkene trolox derivatives within the scope of the invention allows for absorption and distribution along the lines of "classical" non-steroidal anti-inflammatory drugs (NSAIDs), but activates cell signaling pathways due to the presence of the nitroalkenyl functional group. This new class of anti-inflammatory compounds exerts a wide range of anti-inflammatory, anti-proliferative and anti-platelet actions by modifying five major signaling pathways: inhibition of NfkB and inflammasome pathways; activation of Nerf2/Keap 1, PPAR-gamma and Heat Shock Response. The nitroalkene trolox derivatives herein described exert all these signaling effects with the advantage of controlling water solubility. Further, the new generation of nitroalkene trolox derivatives are not as susceptible to beta oxidation or metabolism via the classical desaturation pathway.

Water solubility of the compounds described herein is modified by the saturated hydrocarbon chain length of the nitro alkene, such that the scope of the invention includes hydrosoluble to hydrophobic nitroalkene trolox derivatives.

One embodiment within the scope of the invention is a compound of Formula I:

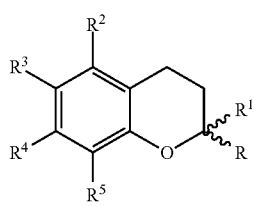

I or a pharmaceutically-acceptable salt thereof, wherein R is a $C_1$-$C_{15}$ nitroalkenyl; $R^1$, $R^2$, $R^4$, and $R^5$ are independently a —H or —CH$_3$; and $R^3$ is selected from the group consisting of —H, —OH, —OBOC, —OCH$_3$, —OBn, —SH, —NO$_2$, —NH$_2$, —CN, a carbonyl, a sulfonate, an amidino.

The compound of Formula I, wherein $R^3$ is selected from the group consisting of —H, a —OH, —OBOC, —OCH$_3$, and —OBn.

Another embodiment includes the compound of Formula I, wherein $R^1$, $R^2$, $R^4$, and $R^5$ are each —CH$_3$.

Another embodiment includes the compound of Formula I, wherein R is a nitrovinyl.

Another embodiment includes the compound of Formula I, wherein $R^3$ is —OH.

Another embodiment is a compound that is 2,5,7,8-tetramethyl-2-(2-nitrovinyl)chroman-6-ol; 2,5,7,8-tetramethyl-2-(2-nitropentenyl)chroman-6-ol; 2,5,7,8-tetramethyl-2-(2-nitro-2-pentenyl)chroman-6-ol; 2,5,7,8-tetramethyl-2-(3-nitro-2-pentenyl)chroman-6-ol; 2,5,7,8-tetramethyl-2-(3-nitro-3-pentenyl)chroman-6-ol; 2,5,7,8-tetramethyl-2-(4-nitro-3-pentenyl)chroman-6-ol; 2,5,7,8-tetramethyl-2-(4-nitro-4-pentenyl)chroman-6-ol; 2,5,7,8-tetramethyl-2-(5-nitro-4-pentenyl)chroman-6-ol; 2,5,7,8-tetramethyl-2-(2-nitrooctenyl)chroman-6-ol; 2,5,7,8-tetramethyl-2-(2-nitro-2-octenyl)chroman-6-ol; 2,5,7,8-tetramethyl-2-(3-nitro-2-octenyl)chroman-6-ol; 2,5,7,8-tetramethyl-2-(3-nitro-3-octenyl)chroman-6-ol; 2,5,7,8-tetramethyl-2-(4-nitro-3-octenyl)chroman-6-ol; 2,5,7,8-tetramethyl-2-(4-nitro-4-octenyl)chroman-6-ol; 2,5,7,8-tetramethyl-2-(5-nitro-4-octenyl)chroman-6-ol; 2,5,7,8-tetramethyl-2-(5-nitro-5-octenyl)chroman-6-ol; 2,5,7,8-tetramethyl-2-(6-nitro-5-octenyl)chroman-6-ol; 2,5,7,8-tetramethyl-2-(6-nitro-6-octenyl)chroman-6-ol; 2,5,7,8-tetramethyl-2-(7-nitro-6-octenyl)chroman-6-ol; 2,5,7,8-tetramethyl-2-(7-nitro-7-octenyl)chroman-6-ol; 2,5,7,8-tetramethyl-2-(8-nitro-7-octenyl)chroman-6-ol; 2,5,7,8-tetramethyl-2-(2-nitrotridecenyl)chroman-6-ol; 2,5,7,8-tetramethyl-2-(2-nitro-2-tridecenyl)chroman-6-ol; 2,5,7,8-tetramethyl-2-(3-nitro-2-tridecenyl)chroman-6-ol; 2,5,7,8-tetramethyl-2-(3-nitro-3-tridecenyl)chroman-6-ol; 2,5,7,8-tetramethyl-2-(4-nitro-3-tridecenyl)chroman-6-ol; 2,5,7,8-tetramethyl-2-(4-nitro-4-tridecenyl)chroman-6-ol; 2,5,7,8-tetramethyl-2-(5-nitro-4-tridecenyl)chroman-6-ol; 2,5,7,8-tetramethyl-2-(5-nitro-5-tridecenyl)chroman-6-ol; 2,5,7,8-tetramethyl-2-(6-nitro-5-tridecenyl)chroman-6-ol; 2,5,7,8-tetramethyl-2-(6-nitro-6-tridecenyl)chroman-6-ol; 2,5,7,8-tetramethyl-2-(7-nitro-6-tridecenyl)chroman-6-ol; 2,5,7,8-tetramethyl-2-(7-nitro-7-tridecenyl)chroman-6-ol; 2,5,7,8-tetramethyl-2-(8-nitro-7-tridecenyl)chroman-6-ol; 2,5,7,8-tetramethyl-2-(8-nitro-8-tridecenyl)chroman-6-ol; 2,5,7,8-tetramethyl-2-(9-nitro-8-tridecenyl)chroman-6-ol; 2,5,7,8-tetramethyl-2-(9-nitro-9-tridecenyl)chroman-6-ol; 2,5,7,8-tetramethyl-2-(10-nitro-9-tridecenyl)chroman-6-ol; 2,5,7,8-tetramethyl-2-(10-nitro-10-tridecenyl)chroman-6-ol; 2,5,7,8-tetramethyl-2-(11-nitro-10-tridecenyl)chroman-6-ol; 2,5,7,8-tetramethyl-2-(11-nitro-11-tridecenyl)chroman-6-ol; 2,5,7,8-tetramethyl-2-(12-nitro-11-tridecenyl)chroman-6-ol; 2,5,7,8-tetramethyl-2-(12-nitro-12-tridecenyl)chroman-6-ol; 2,5,7,8-tetramethyl-2-(13-nitro-12-tridecenyl)chroman-6-ol, or a physiologically acceptable salt thereof.

Another embodiment is the compound (2S)-2,5,7,8-tetramethyl-2-[(E)-2-nitrovinyl]chroman-6-ol or a physiologically acceptable salt thereof.

Another embodiment includes the compound of Formula I, wherein R is a 2-nitrovinyl and the absolute configuration of the chiral carbon adjacent the oxygen atom on the chromanol ring structure is (S).

Another embodiment includes the compound of Formula I, wherein R is a 2-nitroalkenyl and the absolute configuration of the chiral carbon adjacent the oxygen atom on the chromanol ring structure is (S).

Another embodiment includes the compound of Formula I, wherein R is a 3-nitroallyl and the absolute configuration of the chiral carbon adjacent the oxygen atom on the chromanol ring structure is (S).

Another embodiment includes the compound of Formula I, wherein R is a 3-nitroalkenyl and the absolute configuration of the chiral carbon adjacent the oxygen atom on the chromanol ring structure is (S).

Another embodiment includes the compound of Formula I, wherein R has a nitroalkenyl disposed at fourth to fifteenth carbon on the $C_4$-$C_{15}$ hydrocarbon tail and the absolute configuration of the chiral carbon adjacent the oxygen atom on the chromanol ring structure is (R).

Another embodiment includes a pharmaceutical composition comprising a compound of Formula I and a carrier.

Another embodiment includes a method of treating inflammation related disorders comprising the steps of administering to a subject in need thereof a therapeutically effective amount of a compound of Formula I:

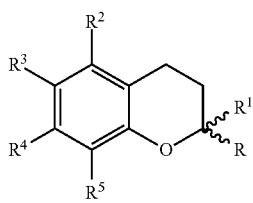

or a pharmaceutically-acceptable salt thereof, wherein R is a $C_1$-$C_{15}$ nitroalkenyl; $R^1$, $R^2$, $R^4$, and $R^5$ are independently a —H or —$CH_3$; and $R^3$ is selected from the group consisting of —H, —OH, —OBOC, —$OCH_3$, —OBn, —SH, —$NO_2$, —$NH_2$, —CN, a carbonyl, a sulfonate, an amidino.

Another embodiment includes a method of treating inflammation related disorders comprising the steps of administering to a subject in need thereof a therapeutically effective amount of a compound of Formula I:

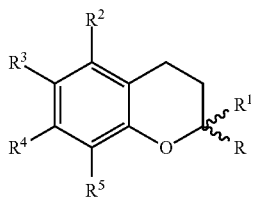

or a pharmaceutically-acceptable salt thereof, wherein R is a $C_1$-$C_{15}$ nitroalkenyl; $R^1$, $R^2$, $R^4$, and $R^5$ are independently a —H or —$CH_3$; and $R^3$ is selected from the group consisting of —H, —OH, —OBOC, —$OCH_3$, —OBn, —SH, —$NO_2$, —$NH_2$, —CN, a carbonyl, a sulfonate, an amidino, wherein the inflammation related disorder is selected from the group consisting of atherosclerosis, obesity, metabolic syndrome, arterial hypertension (HTA), acne vulgaris, asthma, autoimmune diseases, autoinflammatory diseases, celiac disease, chronic prostatitis, glomerulonephritis, inflammatory bowel diseases, pelvic inflammatory disease, reperfusion injury, rheumatoid arthritis, sacroidosis, transplant rejection, vasculitis, and interstitial cystitis.

Another embodiment includes a method of treating inflammation related disorders comprising the steps of administering to a subject in need thereof a therapeutically effective amount of a compound of Formula I:

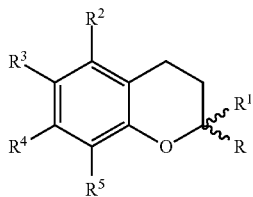

or a pharmaceutically-acceptable salt thereof, wherein R is a nitro-alcohol or a $C_1$-$C_{15}$ nitroalkenyl; $R^1$, $R^2$, $R^4$, and $R^5$ are independently a —H or —$CH_3$; and $R^3$ is selected from the group consisting of —H, —OH, —OBOC, —$OCH_3$, —OBn, —SH, —$NO_2$, —$NH_2$, —CN, a carbonyl, a sulfonate, an amidino, wherein the inflammation related disorder is atherosclerosis.

Another embodiment includes a method of treating inflammation related disorders comprising the steps of administering to a subject in need thereof a therapeutically effective amount of (E)-2,5,7,8-tetramethyl-2-(2-nitrovinyl) chroman-6-ol or a physiologically acceptable salt thereof.

Another embodiment includes a method of preparing a compound of formula I

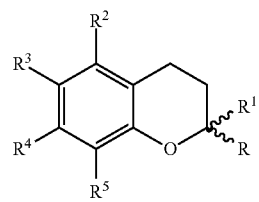

or a pharmaceutically-acceptable salt thereof, wherein R is a nitro-alcohol or a $C_1$-$C_{15}$ nitroalkenyl;
$R^1$ is $CH_3$;
$R^2$, $R^4$, and $R^5$ is —H; and
$R^3$ is —OH, a carbonyl, a sulfonate, an amidino which comprises treating a compound of Formula II

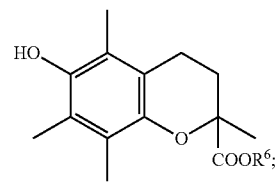

wherein $R^6$ is a $C_{1-6}$ alkyl with a protective group (Pro) in a polar aprotic solvent in the present of a nucleophilic catalyst to yield a compound of Formula III

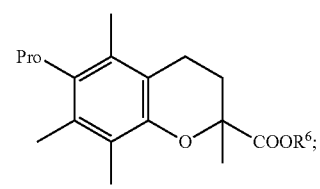

followed by treating the compound of Formula III with a reducing agent in a polar aprotic solvent to reduce the $COOR^6$ group to a primary alcohol of Formula IV

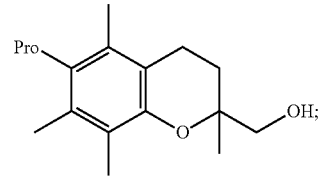

followed by treating the compound of Formula IV with an oxidizing catalyst and oxidizing reagent in a polar aprotic solvent to produce the compound of Formula V

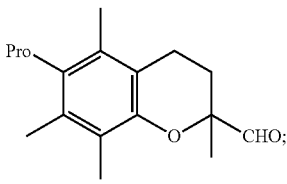

and followed by treating the compound of Formula V with a compound of Formula VI

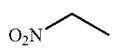

in the presence of a catalytic base to produce a compound of Formula VII

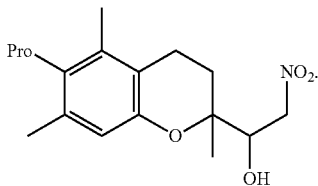

DETAILED DESCRIPTION

Figure 1A:
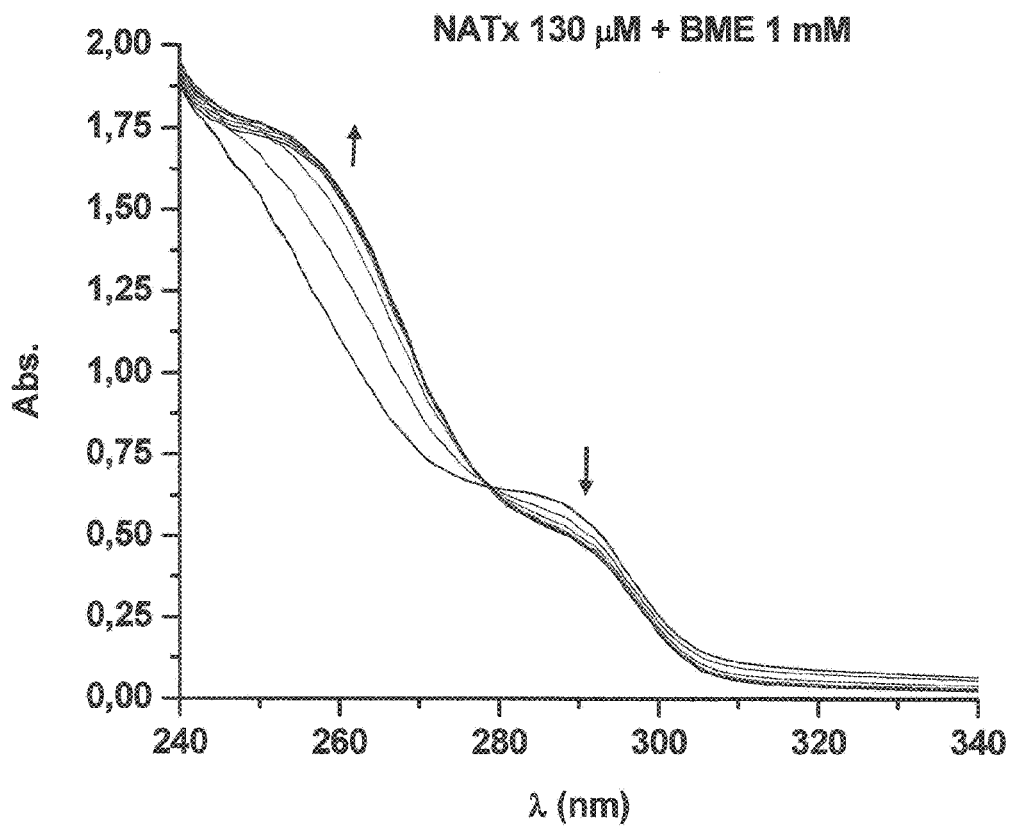
FIGS. 1A and 1B demonstrate changes in absorption spectra characteristic of adduct formation between sulfur moieties of β-mercaptoethanol with the nitro vinyl β-carbon via Michael addition.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 5% of the numerical value of the number with which it is being used. Therefore, about 50% means in the range of 45%-55%.

"Administering" when used in conjunction with a therapeutic means to administer a therapeutic directly to a subject, whereby the agent positively impacts the target. "Administering" a composition may be accomplished by, for example, injection, oral administration, topical administration, or by these methods in combination with other known techniques. Such combination techniques include heating, radiation, ultrasound and the use of delivery agents. When a compound is provided in combination with one or more other active agents (e.g. other anti-atherosclerotic agents such as the class of statins), "administration" and its variants are each understood to include concurrent and sequential provision of the compound or salt and other agents.

By "pharmaceutically acceptable" it is meant the carrier, diluent, adjuvant, or excipient must be compatible with the other ingredients of the formulation and not deleterious to the recipient thereof.

"Composition" as used herein is intended to encompass a product comprising the specified ingredients in the specified amounts, as well as any product which results, directly or indirectly, from combination of the specified ingredients in the specified amounts. Such term in relation to "pharmaceutical composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound o the present invention and a pharmaceutically acceptable carrier.

As used herein, the term "agent," "active agent," "therapeutic agent," or "therapeutic" means a compound or composition utilized to treat, combat, ameliorate, prevent or improve an unwanted condition or disease of a patient. Furthermore, the term "agent," "active agent," "therapeutic agent," or "therapeutic" encompasses a combination of one or more of the compounds of the present invention.

A "therapeutically effective amount" or "effective amount" of a composition is a predetermined amount calculated to achieve the desired effect, i.e., to inhibit, block, or reverse the activation, migration, proliferation, alteration of cellular function, and to preserve the normal function of cells. The activity contemplated by the methods described herein includes both medical therapeutic and/or prophylactic treatment, as appropriate, and the compositions of the invention may be used to provide improvement in any of the conditions described. It is also contemplated that the compositions described herein may be administered to healthy subjects or individuals not exhibiting symptoms but who may be at risk of developing a particular disorder. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the chosen dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refer to both therapeutic treatment and prophylactic or preventative measures, wherein the object is to prevent or slow down (lessen) an undesired physiological condition, disorder, or disease, or to obtain beneficial or desired clinical results. For the purposes of this invention, beneficial or desired results include, but are not limited to, alleviation of symptoms; diminishment of the extent of the condition, disorder, or disease; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease. Treatment includes prolonging survival as compared to expected survival if not receiving treatment.

Among its many embodiments the present invention provides a compound of Formula I

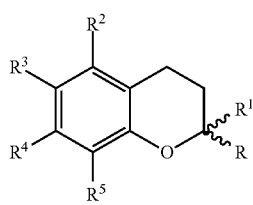

I or a pharmaceutically-acceptable salt thereof, wherein R is a nitro-alcohol or a $C_1$-$C_{15}$ nitroalkenyl; $R^1$, $R^2$, $R^4$, and $R^5$ are independently a —H or —$CH_3$; and $R^3$ is selected from the group consisting of —H, —OH, —OBoc, —$OCH_3$, —OBn, —SH, —$NO_2$, —$NH_2$, —CN, a carbonyl, a sulfonate, an amidino.

Also included in the family of compounds of Formula I are the stereoisomers thereof. Compounds of the present invention can possess one or more asymmetric carbon atoms and are thus capable of existing in the form of optical isomers as well as in the form of racemic or nonracemic mixtures thereof. Accordingly, some of the compounds of this invention may be present in racemic mixtures which are also included in this invention.

The optical isomers can be obtained by resolution of the racemic mixtures according to conventional processes, for example by formation of diastereoisomeric salts by treatment with an optically active base and then separation of the mixture of diastereoisomers by crystallization, followed by liberation of the optically active bases from these salts. Another method calls for chiral separation of the enantiomers with the use of a chiral chromatography column optimized to maximize the separation of the enantiomers. Optimization of the chromatographic method of chiral resolution is routine for one of ordinary skill in the art. Yet another method for isolating optical isomers is by distillation, crystallization or sublimation if a physical property of the enantiomers is different. The optically active compounds of Formula I can also be obtained by utilizing optically active starting materials. The isomers may be in the form of a free acid, a free base, an ester or a salt.

Also included in the family of compounds of Formula I and the stereoisomers are the pharmaceutically-acceptable salts thereof. The term "pharmaceutically-acceptable salts" embraces salts commonly used to form alkali metal salts and to form additional salts of free acids or free bases. The nature of the salt is not critical, provided that it is pharmaceutically-acceptable. Suitable pharmaceutically-acceptable acid addition salts of compounds of Formula I may prepared from an inorganic acid or from an organic acid. Examples of such inorganic acids are hydrochloric, hydrobromic, hydroiodic, nitric, carbonic, sulfuric and phosphoric acid. Appropriate organic acids may include aliphatic, cycloaliphatic, aromatic, araliphatic, heterocyclic, carboxylic and sulfonic classes of organic acids. Examples of such organic acids include formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, 4-hydrobenzoic, phylacetic, mandelic, embonic, methanesulfonic, ethanesulfonic, benzenesulfonic, pantothenic, 2-hydroxyethanesulfonic, toluenesulfonic, sulfanilic, cyclohyexylaminosuflonic, stearic, algenic, β-hydrobutyric, galactaric and galacturnoic acid. Suitable pharmaceutically-acceptable base addition salts of compounds of Formula I include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, triethylamine, trimethylamine. All the listed salts of the corresponding compound of the invention may be prepared by conventional means known to one of ordinary skill in the art. One example of a conventional method of salt formation is by reacting the appropriate acid or base with the compounds of Formula I at various mole ratios. Another method is by using different mole ratios of the appropriate acid or base in various solvent systems to control the concentration of the dissociated species of the compounds of Formula I to maximize salt formation. The present invention also contemplates crystalline forms of the salts described herein.

Crystalline forms of the compounds of Formula I, may also include but are not limited to hydrates, solvates, and co-crystals. Crystalline solvates include solvents including but not limited to the following: MeOH, EtOH, AcOH, EtOEt, AcOEt, acetone, DMSO, DMF, MeCN, $CH_2Cl_2$, $CHCl_3$, $CCl_4$, dioxane, THF, benzene, toluene, p-xylene, and hexane.

Crystalline hydrates and solvates may be stoichiometric as according to the mole ratio of the water or organic solvent molecule to the compound or salt thereof. The crystalline hydrate may also be non-stoichiometric depending on the conditions of the unit cell which result in a thermodynamically or kinetically stable crystal. Crystalline salts and co-crystals may also be stoichiometric or non-stoichiometric for reasons stated above. One of skill in the art of crystallography understands that the components in the unit cell of a crystal may or may not be stoichiometric depending on the conditions which stabilize the crystal.

Administration and Compositions

The Compounds of Formula I Can be Administered to a Patient

The compounds and pharmaceutically-acceptable salts thereof can be administered by means that produces contact of the active agent with the agent's site of action. They can be administered by conventional means available for use in conjunction with pharmaceuticals in a dosage range of 0.001 to 1000 mg/kg of mammal (e.g. human) body weight per day in a single dose or in divided doses. One dosage range is 0.01 to 500 mg/kg body weight per day orally in a single dose or in divided doses. Administration can be delivered as individual therapeutic agents or in a combination of therapeutic agents. They can be administered alone, but typically are administered with a pharmaceutically acceptable excipient selected on the basis of the chosen route of administration and standard pharmaceutical practice.

Compounds can be administered by one or more ways. For example, the following routes may be utilized: oral, parenteral (including subcutaneous injections, intravenous, intramuscular, intrasternal injection or infusion techniques), inhalation, buccal, sublingual, or rectal, in the form of a unit dosage of a pharmaceutical composition containing an effective amount of the compound and optionally in combination with one or more pharmaceutically-acceptable excipients such as stabilizers, anti-oxidants, lubricants, bulking agents, fillers, carriers, adjuvants, vehicles, diluents and other readily known excipients in standard pharmaceutical practice.

Liquid preparations suitable for oral administration (e.g. suspensions, syrups, elixirs and other similar liquids) can employ media such as water, glycols, oils, alcohols, and the like. Solid preparations suitable for oral administration (e.g. powders, pills, capsules and tablets) can employ solid excipients such as starches, sugars, kaolin, lubricants, binders, disintegrating agents, antioxidants and the like.

Parenteral compositions typically employ sterile water as a carrier and optionally other ingredients, such as solubility aids. Injectable solutions can be prepared, for example, using a carrier comprising a saline solution, a glucose solution or a solution containing a mixture of saline and glucose. Further guidance for methods suitable for use in preparing pharmaceutical compositions is provided in *Remington: The Science and Practice of Pharmacy,* $21^{st}$ edition (Lippincott Williams & Wilkins, 2006).

Therapeutic compounds can be administered orally in a dosage range of about 0.001 to 1000 mg/kg of mammal (e.g. human) body weight per day in a single dose or in divided doses. One dosage range is about 0.01 to 500 mg/kg body weight per day orally in a single dose or in divided doses. For oral administration, the compositions can be provided in the form of tablets or capsules containing about 1.0 to 500 mg of the active ingredient, particularly about 1, 5, 10, 15, 20, 25, 50, 75, 100, 150, 200, 250, 300, 400, 500, and 750 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In view of the factors affecting the specific dose level and frequency it is contemplated that the dose frequency can range from multiple doses daily to monthly dosages. The preferred dose frequency ranges from twice a day to every two weeks. A more preferred dose frequency ranges from twice a day to weekly. A most preferred dose frequency ranges from twice a day to twice a week.

In the methods of various embodiments, pharmaceutical compositions including the active agent can be administered to a subject in an "effective amount." An effective amount may be any amount that provides a beneficial effect to the patient, and in particular embodiments, the effective amount is an amount that may 1) prevent the subject from experiencing one or more adverse effects associated with a administered agents, such as those used to diagnose, identify, and treat medical conditions, 2) reduce side effects experienced by the subject as a result of a medical therapy or reduce the side effects known to result from such therapies, and/or 3) eliminate side effects resulting from a medical treatment experienced by the subject prior to administration of the active agent or eliminate the side effects known to result from such treatment.

Pharmaceutical formulations containing the compounds of the invention and a suitable carrier can be in various forms including, but not limited to, solids, solutions, powders, fluid emulsions, fluid suspensions, semi-solids, and dry powders including an effective amount of an the active agent of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, *Modern Pharmaceutics,* Banker & Rhodes, Marcel Dekker, Inc. (1979); and *Goodman & Gilman's, The Pharmaceutical Basis of Therapeutics,* 6th Edition, MacMillan Publishing Co., New York (1980) both of which are hereby incorporated by reference in their entireties can be consulted.

Other embodiments of the invention include the active agent prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

In another exemplary embodiment, an oily preparation of an active agent prepared as described above may be lyophilized to form a solid that may be mixed with one or more pharmaceutically acceptable excipient, carrier or diluent to form a tablet, and in yet another embodiment, the active agent may be crystallized to from a solid which may be combined with a pharmaceutically acceptable excipient, carrier or diluent to form a tablet.

The means and methods for tableting are known in the art and one of ordinary skill in the art can refer to various references for guidance. For example, *Pharmaceutical Manufacturing Handbook: Production and Processes*, Shayne Cox Gad, John Wiley & Sons, Inc., Hoboken, N.J. (2008), which is hereby incorporated by reference in its entirety, can be consulted.

Further embodiments which may be useful for oral administration of the active agent include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt. Other suitable diluents include, but are not limited to those described below:

Vegetable oil: The vegetable oil may be hydrogenated or unhydrogenated. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chemicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from CJ Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, *Handbook of Pharmaceutical Excipients*, (2006), 5th ed., which is incorporated herein by reference in its entirety. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

Mineral oils: As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

Castor oils: As used herein, the term "castor oil," refers to a compound formed from the ethoxylation of castor oil, wherein at least one chain of polyethylene glycol is covalently bound to the castor oil. The castor oil may be hydrogenated or unhydrogenated. Synonyms for polyethoxylated castor oil include, but are not limited to polyoxyl castor oil, hydrogenated polyoxyl castor oil, mcrogolglyceroli ricinoleas, macrogolglyceroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-719 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine). Other suitable polyoxyethylene castor oil derivatives include those listed in R. C. Rowe and P. J. Shesky, *Handbook of Pharmaceutical Excipients*, (2006), 5th ed., which is incorporated herein by reference in its entirety.

Sterol: As used herein, the term "sterol" refers to a compound, or mixture of compounds, derived from the ethoxylation of sterol molecule. Suitable polyethoyxlated sterols include, but are not limited to, PEG-24 cholesterol ether, Solulan™ C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™ BPS-20 (available from Nikko); and PEG-30 soya sterol, Nikkol™ BPS-30 (available from Nikko).

Polyethylene glycol: As used herein, the term "polyethylene glycol" or "PEG" refers to a polymer containing ethylene glycol monomer units of formula —O—$CH_2$—$CH_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

Propylene glycol fatty acid ester: As used herein, the term "propylene glycol fatty acid ester" refers to an monoether or diester, or mixtures thereof, formed between propylene glycol or polypropylene glycol and a fatty acid. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates: Capryol™ PGMC and 90 (available from Gatefosse); and propylene glycol dicaprylocaprates: Labrafac™ PG (available from Gatefosse).

Stearoyl macrogol glyceride: Stearoyl macrogol glyceride refers to a polyglycolized glyceride synthesized predominately from stearic acid or from compounds derived predominately from stearic acid, although other fatty acids or compounds derived from other fatty acids may used in the synthesis as well. Suitable stearoyl macrogol glycerides include, but are not limited to, Gelucire® 50/13 (available from Gattefossé).

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

Exemplary excipients or carriers for use in solid and/or liquid dosage forms include, but are not limited to:

Sorbitol: Suitable sorbitols include, but are not limited to, PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, *Handbook of Pharmaceutical Excipients*, (2006), 5th ed., which is incorporated herein by reference in its entirety.

Disintegrant: The disintegrant may include one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

Still further embodiments of the invention include the active agent administered in combination with other active such as, for example, adjuvants, protease inhibitors, or other compatible drugs or compounds where such combination is seen to be desirable or advantageous in achieving the desired effects of the methods described herein.

Other embodiments of the present invention include a pharmaceutical composition comprising an effective amount of the active agent and one or more pharmaceutically acceptable excipient. Other embodiments include a pharmaceutical composition comprising an effective amount of pharmaceutically-acceptable salts of the active agent. Other embodiments include a pharmaceutical composition comprising an effective amount of pharmaceutically-acceptable salts of active agent and a pharmaceutically-acceptable excipient.

In yet other embodiments, the active agent may be combined with one or more secondary agents.

General Synthetic Procedures

The general synthetic routes by which the derivatives of trolox are obtained are shown in Schemes 1, 2 and 3.

Scheme 1

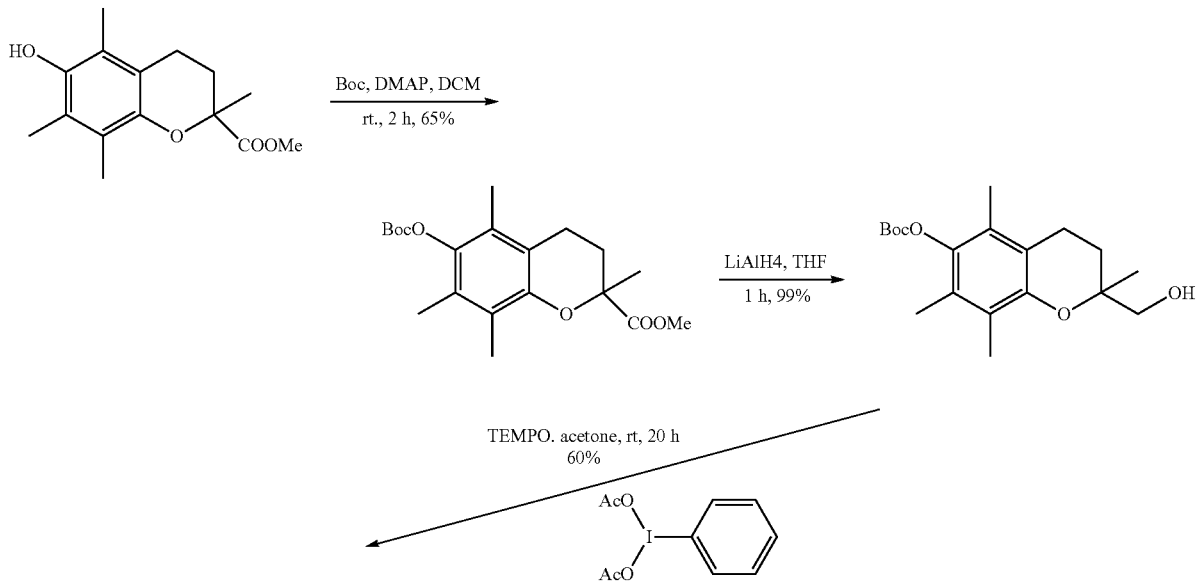

-continued

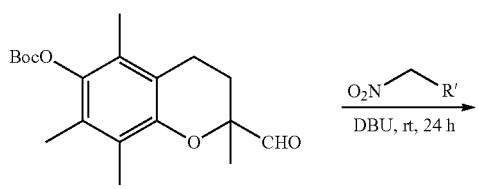
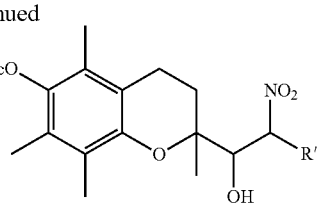

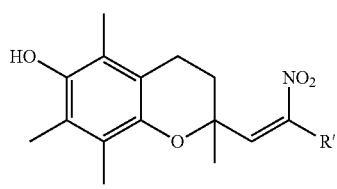
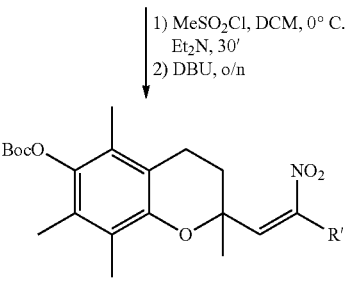

Scheme 1 illustrates preparation of nitrated trolox derivatives with vinyl nitro groups of at the trolox end of the hydrocarbon chain. This type of vinyl nitro is also referred to as the initial vinyl nitro group herein. In Scheme 1, the methyl ester starting material can be formed by reacting commercially available Trolox (Sigma-Aldrich) with methanol and an acid such as sulfuric acid. The reaction proceeds with the attachment of a protective group such as tert-butyloxycarbonyl (Boc). The methyl ester is then reduced to a primary alcohol and subsequently oxidized to produce the aldehyde derivative. The beta-nitro alcohol intermediate is produced via condensation of the aldehyde derivative with a primary nitroalkane, wherein R' is hydrogen or a $C_1$-$C_{11}$ carbon, in the presence of a base (Henry reaction). The base used in the Henry reaction can be DBU, imidazole, or any catalytic base known to a person of ordinary skill in the art.

Dehydration of the beta-nitro alcohol followed by Boc deprotection produces the desired product.

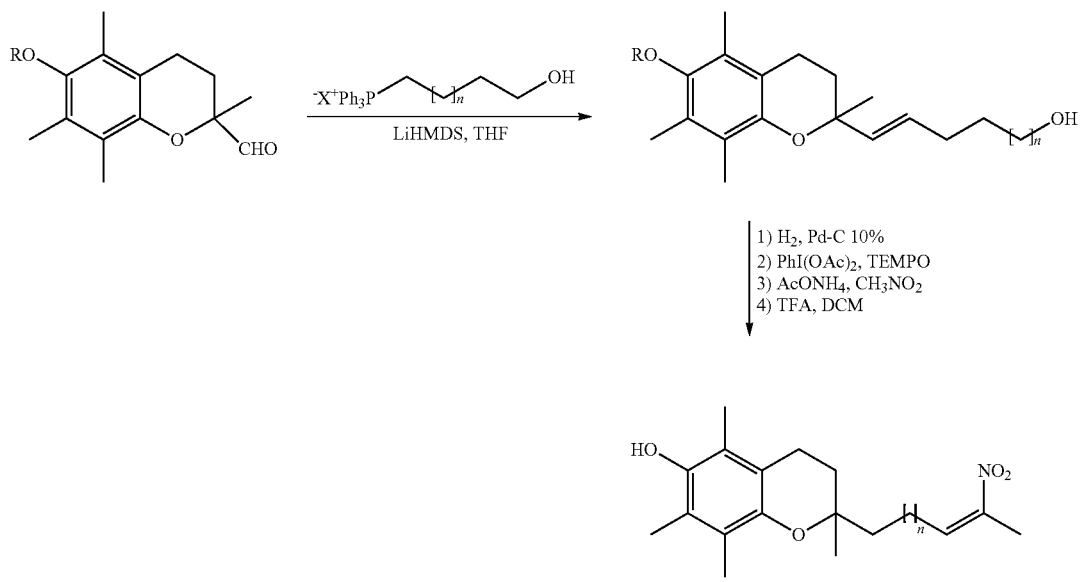

This scheme represents a proposed synthesis for the trolox derivatives containing a vinyl nitro group at the $C_{n-1}$ carbon. This vinyl nitro is also referred to as the terminal nitro vinyl group herein. From the aldehyde derivative produced in the manner shown in Scheme 1, a Wittig reaction with LIHMDS as the base and a hydroxyl-phosphonium salt (prepared as described elsewhere) with the appropriate carbon length, render the alkene with a terminal hydroxyl group. After alkene reduction with $H_2$ and Pd/C, alcohol oxidation to aldehyde, nitroaldolic reaction with nitromethane using ammonium acetate and Boc deprotection, render the desire products.

Scheme 3

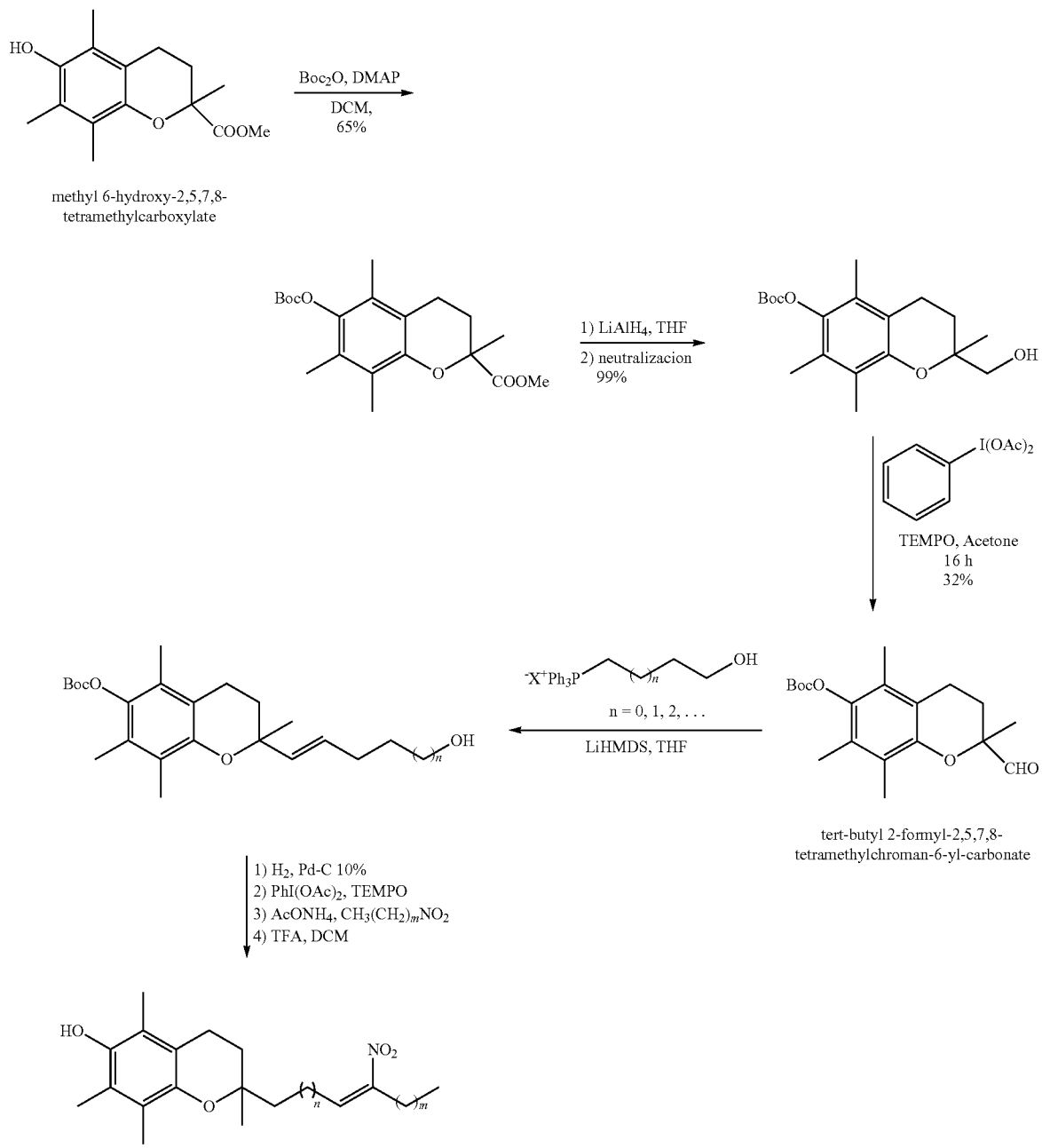

Scheme 3 illustrates a general reaction for preparing embodiments with the scope of contemplated compounds wherein the vinyl nitro group is disposed within the hydrocarbon tail otherwise called an intermediate vinyl nitro group herein.

From tert-butyl 2-formyl-2,5,7,8-tetramethylchroman-6-yl carbonate, synthesized as previously described (the intermediate from the synthesis of compounds with the nitro vinyl group at the beginning of hydrocarbon chain nearest the chromanol base structure). ω-Hydroxyalkyltriphenylphosphonium bromides were synthesized as described in literature (Lei, H., and Atkinson, J. Synthesis of phytyl- and chroman-derivatized photoaffinity labels based on alpha-tocopherol. *J Org Chem* 2000, 65:2560-2567).

EXAMPLES

The following examples contain detailed methods of preparing compounds of Formula I. These detailed descriptions serve to exemplify the above general synthetic schemes which form part of the invention. These detailed descriptions are presented for illustrative purposes only and are not intended as a restriction on the scope of the invention. All parts are by weight and temperatures are in Degrees Celsius unless otherwise indicated. All compounds showed NMR spectra consistent with their assigned structures.

Example 1

(±)-2,5,7,8-tetramethyl-2-[(E)-2-nitrovinyl]chroman-6-ol (NATx0)

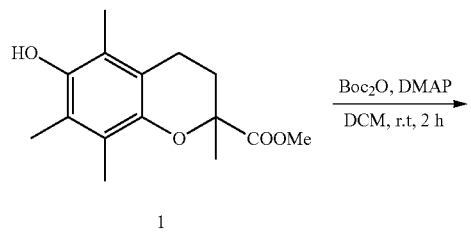

1

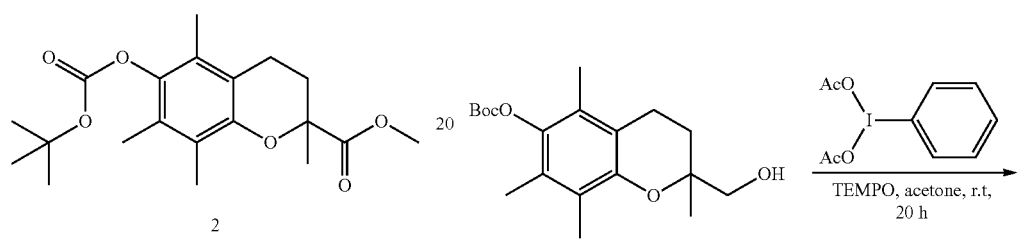

2

Step 1. Preparation of the protected intermediate 2 (methyl 6-((tert-butoxycarbonyl)oxy)-2,5,7,8-tetramethyl-chroman-2-carboxylate)

To a methyl ester 1 (1.5 g, 5.70 mmol) solution in DCM under N2 flux, di-tert-butyl dicarbonate (1.1 g, 5.11 mmol) and a nucleophilic catalyst, DMAP (0.07 g, 0.57 mmol), were added. After 2 hours of agitation at room temperature, reaction was stopped, solvent was evaporated, ethyl acetate was added (20 mL) and then washed with HCl 10% (50 mL) and saturated NaHCO$_3$ (50 mL). The resulting organic layers were dried with Na$_2$SO$_4$, filtered and the solvent was evaporated under reduced pressure. Purification by column chromatography in SiO$_2$ and hexane:ethyl acetate 7:3 as mobile phase rendered the desired product as a white solid (1.3 g, 65%). $^1$H NMR (400 MHz, CDCl$_3$): δ 3.70 (s, 3 H), 2.69 (m, 1 H), 2.53 (m, 1 H), 2.45 (m, 1 H), 2.18 (s, 3 H), 2.11 (s, 3 H), 2.02 (s, 3H), 1.88 (m, 1 H), 1.62 (s, 3H), 1.57 (s, 9H).

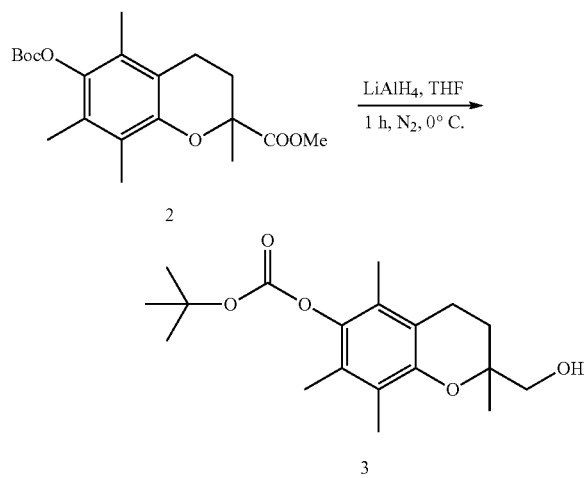

Step 2. Preparation of 3 (6-((tert-butoxycarbonyl)oxy)-2,5,7,8-tetramethylchroman-2-methanol)

To a suspension of a reducing agent, LiAlH$_4$ (1.8 mmol, 0.07 g), in dry THF (2 mL) cooled to 0° C. in a water-salt bath under nitrogen atmosphere, 2 (1.6 mmol, 0.6 g) dissolved in 4 mL of dry THF was added dropwise. The reaction mixture was stirred at 0° C. for 45 min and poured into a saturated aqueous solution of NH$_4$Cl (6 mL) and extracted with EtOAc (3×10 mL). The combined organic layers were washed with water (1×10 mL), brine (1×10 mL), dried (Na$_2$SO$_4$), filtered and the solvent was evaporated under reduced pressure, to give a white solid (0.50 g, 94%). No further purification was required. $^1$H NMR (300 MHz, CDCl$_3$): δ 3.70 (m, 2 H, 4 H), 2.70 (m, 2 H), 2.11 (s, 3 H), 2.10 (s, 3 H), 2.07 (s, 3 H), 2.00 (m, 1 H), 1.91 (t, 1 H), 1.76 (m, 1 H), 1.58 (s, 9 H), 1.25 (s, 3 H).

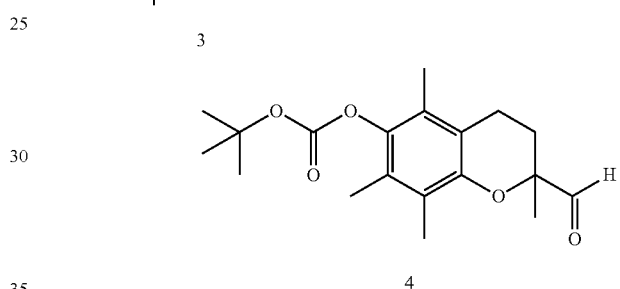

3

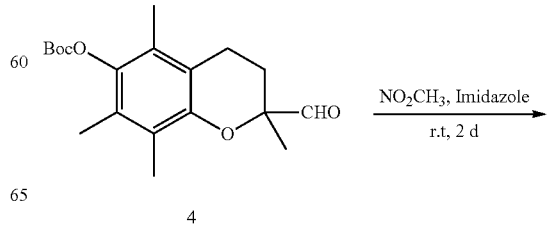

4

Step 3. Preparation of 4 (6-((tert-butoxycarbonyl)oxy)-2,5,7,8-tetramethylchroman-2-carbaldehyde)

To a solution of 3 (1.5 mmol, 0.50 g) an oxidizing catalyst, TEMPO (0.32 mmol, 0.047 g), in acetone, and (diacetoxyiodo)benzene (2.0 mmol, 0.65 g) was added. After 20 h of stirring at room temperature the reaction mixture was poured into water (10 mL) and extracted with diethyl ether (4×10 mL). The organic layers were dried with Na$_2$SO$_4$, filtered and the solvent was evaporated under reduced pressure. The liquid residue was loaded onto a silica gel flash column and eluted with hexane:ethyl acetate 95:5 to afford a white solid (0.16 g, 32%). $^1$H NMR (400 MHz, CDCl$_3$): δ 9.65 (s, 1 H), 2.67 (m, 2 H), 2.31 (m, 1H), 2.22 (s, 3 H), 2.13 (s, 3 H), 2.03 (s, 3 H), 1.87 (m, 1 H), 1.58 (s, 9 H), 1.42 (s, 3 H).

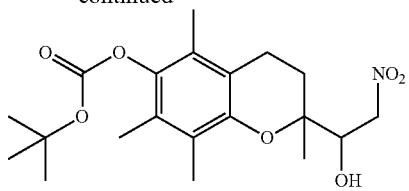

5

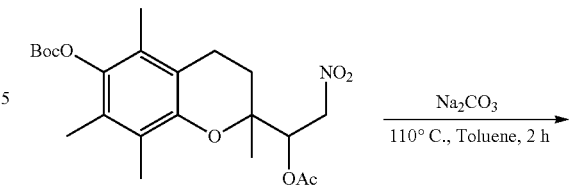

Step 4. Preparation of 5 (6-((tert-butoxycarbonyl)oxy)-2-(1-hydroxy-2-nitroethyl)-2,5,7,8-tetramethylchroman)

To a solution of imidazole (1.3 mmol, 0.09 g) in nitromethane (3.5 mL, 65 mmol), 4 (0.65 mmol, 0.16 g) was added. After 2 days of stirring at room temperature, solvent was evaporated under reduced pressure and the crude product was poured into brine and extracted with ethyl acetate. The organic layers were dried with $Na_2SO_4$, filtered and the solvent was evaporated under reduced pressure. The residue was loaded onto a silica gel flash column and eluted with hexane: ethyl acetate 8:2 to afford a white solid (0.12 g, 60%). $^1$H NMR (400 MHz, $CDCl_3$): δ 4.81 (m, 1 H), 4.61 (m, 1 H), 4.44 (m, 1 H), 2.84 (d, J=4 Hz, 1 H), 2.74 (m, 2 H), 2.11 (s, 3H), 2.09 (s, 3H), 2.07 (s, 3 H), 1.99 (m, 2 H), 1.58 (s, 9 H), 1.26 (s, 3 H). $^{13}$C NMR (400 MHz, $CDCl_3$): δ 77, 73, 28, 27, 20, 19, 13.

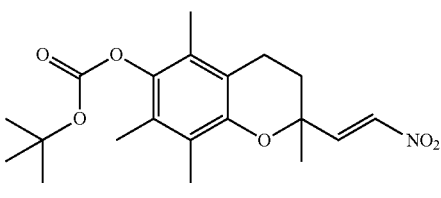

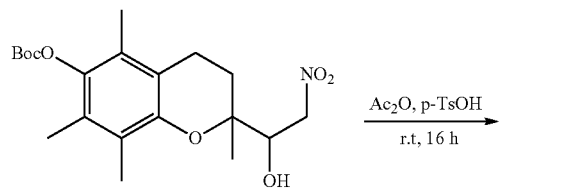

Step 5. Preparation of 6 (2-(1-acetoxy-2-nitroethyl)-6-((tert-butoxycarbonyl)oxy)-2,5,7,8-tetramethylchroman)

A solution of 5 (0.092 mmol, 0.036 mg) in acetic anhydride (2.9 mmol, 0.28 mL) and catalytic amount of a sulphonic acid, p-toluensulphonic acid, was kept in agitation for 16 h under $N_2$ flow. Then, water (10 mL) was added and agitation continued for 10 minutes more to remove acetic anhydride excess as acetic acid. Product was extracted with diethyl ether (4 mL) and the organic layer was washed with water (3×5 mL). The organic layer was dried with $Na_2SO_4$, filtered and the solvent was evaporated under reduced pressure to obtain a white solid (0.037 g, 93%). $^1$H NMR (400 MHz, $CDCl_3$): δ 5.85 (m, 1 H), 4.88 (m, 1 H), 4.74 (m, 1 H), 2.80 (m, 1 H), 2.65 (m, 1 H), 2.14 (s, 3H), 2.10 (s, 3H), 2.08 (s, 3H), 2.06 (s, 3H), 1.90 (m, 2H), 1.57 (s, 9H), 1.29 (s, 3H).

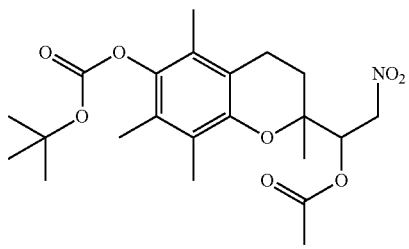

Step 6. Preparation of 7 (6-((tent-butoxycarbonyl)oxy)-2,5,7,8-tetramethyl-2-[(E) 2-nitrovinyl]chroman)

Reactants were dissolved in dry toluene and the mixture was heated at 110° C. for 2 h. After the reaction mixture reached ambient temperature, it was poured into brine (10 mL) and extracted with diethyl ether (3×5 mL) to obtain a yellow solid (0.03 g, 94%) with no further purification. $^1$H NMR (400 MHz, $CDCl_3$): δ 7.28 (d, J=12 Hz, 1H), 7.02 (d, J=12 Hz, 1H), 2.76 (m, 1H), 2.57 (m, 1H), 2.17 (s, 3H), 2.13 (s, 3H), 2.07 (s, 3H), 2.05 (m, 2H), 1.57 (s, 9H), 1.28 (s, 3H). $^{13}$C-NMR (400 MHz, $CDCl_3$): δ 152.1, 147.9, 144.6, 141.8, 139.6, 127.9, 125.6, 122.8, 116.7, 82.96, 74.06, 31.44, 30.33, 29.72, 27.69, 25.87, 20.51, 12.75, 11.91, 11.86. MS ($EI^+$): m/z (%): 377 ($M^-$, 6), 277 (100), 164 (55).

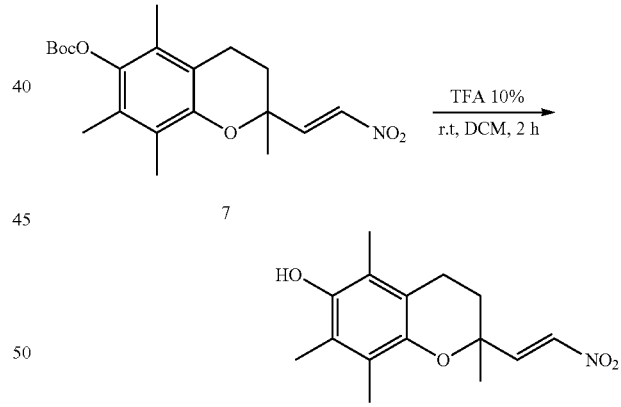

Step 7. Preparation of NATx0

To a solution of 7 (0.03 g, 0.08 mmol) in DCM, TFA (0.135 mL, 1.75 mmol) was added and the reaction was stirred for 2 h at room temperature. Then, the reaction mixture was washed with $NaHCO_3$ sat. (5 mL) and brine (5 mL). The organic layer was dried with $Na_2SO_4$, filtered and the solvent was evaporated under reduced pressure. The residue was loaded onto a silica gel flash column and eluted with hexane:ethyl acetate 8:2 to afford a yellow solid (0.066 g, 30%). $^1$H NMR (400 MHz, $CDCl_3$): δ 7.28 (d, J=13.6 Hz, 1H), 6.99 (d, J=13.2 Hz, 1H), 4.31 (s, 1H), 2.77 (m, 1H), 2.56 (m, 1H), 2.20 (s, 3H), 2.19 (s, 3H), 2.11 (s, 3H), 2.09 (m, 1H), 2.00 (m, 1H), 1.53 (s, 3H). $^{13}$C-NMR (400 MHz, $CDCl_3$): δ 145.5, 144.8, 144.2, 139.6, 122.3, 121.7, 118.6, 116.6, 73.71, 31.80, 26.04, 20.75, 12.23, 11.85, 11.32. MS (EI⁺): m/z (%): 277 (M⁺, 71), 164 (100), 136 (29), 121 (28).

Example 2

(±)-2,5,7,8-tetramethyl-2-[(E)-2-nitropent-1-en-1-yl]chroman-6-ol (NATx5)

Steps 1-3 of Example 1 are repeated to prepare 4 (6-((tert-butoxycarbonyl)oxy)-2,5,7,8-tetramethylchroman-2-carbaldehyde).

Step 4. Preparation of tert-butyl (2,5,7,8-tetramethyl-2-[(E)-2-nitropent-1-en-1-yl]chroman-6-yl) carbonate.

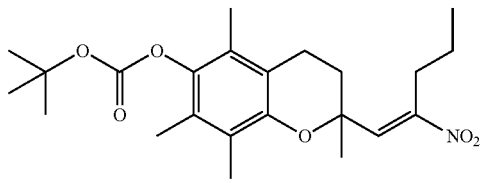 [SMILES: CCC/C(=C\C1(C)CCc2c(C)c(OC(=O)OC(C)(C)C)c(C)c(C)c2O1)[N+](=O)[O-]]

A mixture of 1-nitrobutane (0.023 g, 0.22 mmol), aldehyde 4 (0.075 g, 0.22 mmol) and DBU (0.1 mL, 0.022 mmol) in acetonitrile (1 mL) was stirred at room temperature for 24 h. The solvent was removed under reduced pressure and the residue was loaded onto a silica gel column (SiO$_2$, Hexane:Ethyl acetate 85:15) to afford the nitrohydroxy product as a diasteromeric mixture (white solid 0.075 g, 81%). MS (EI⁺): m/z (%): 437 (M⁺, 4), 337 (22), 234 (39), 205 (100), 149 (21), 57 (94). HRMS: m/z [M⁺] calcd. for C$_{23}$H$_{35}$NO$_7$: 437.2414, found: 437.2421.

To nitrohydroxy intermediate(0.07 g, 0.16 mmol) in dry DCM (3 mL), methanesulfonyl chloride (0.037 g, 0.32 mmol) and triethylamine (0.058 mL, 0.42 mmol) were added in an ice-water bath. After 2 h, complete formation of mesyl derivatives (as diasteromic mixture) was observed. Then DBU (0.06 g, 0.4 mmol) was added and reaction was stirred overnight. Water was added (20 mL) and compound was extracted with ethyl acetate (3×5 mL), dried with Na$_2$SO$_4$, filtered and solvent removed under reduced pressure. The residue was loaded onto a silica gel column (SiO$_2$, Hexane:Ethyl acetate 85:15) to afford the desire product as a yellow oil (0.046 g, 69%). ¹H-NMR (CDCl$_3$, 500 MHz): δ=6.93 (s, 1H); 2.67 (t, J=10 Hz, 2H), 2.60 (m, 1H), 2.53 (m, 1H), 2.07 (s, 3H), 2.02 (s, 3H), 1.97 (m, 1H), 1.95 (s, 3H), 1.84 (m, 1H), 1.47 (s, 9H), 1.46 (s, 3H), 1.40 (m, 1H), 1.20 (m, 1H), 0.82 (t, J=10 Hz, 3H). ¹³C-NMR (CDCl$_3$, 500 MHz): δ 153.1, 152.1, 148.4, 141.7, 137.4, 128.2, 125.7, 122.7, 117.2, 82.88, 74.66, 32.90, 28.22, 27.62, 26.41, 21.62, 20.77, 13.93, 12.77, 12.08, 11.91. MS (EI⁺): m/z (%): 419 (M⁺, 2.04), 319 (29.04), 164.08 (19.62), 57.07 (100). HRMS: m/z [M⁺] calcd. for C$_{23}$H$_{33}$NO$_6$: 419.2308, found: 419.2308.

Step 5. Preparation of NATx5.

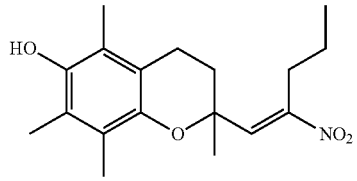 [SMILES: CCC/C(=C\C1(C)CCc2c(C)c(O)c(C)c(C)c2O1)[N+](=O)[O-]]

To a solution of tert-butyl (2,5,7,8-tetramethyl-2-[(E)-2-nitropent-1-en-1-yl)chroman-6-yl) carbonate (0.02 g, 0.048 mmol) in DCM (0.8 mL), TFA (0.081 mL, 1.05 mmol) was added and was stirred for 2 h at room temperature. Then, the reaction mixture was washed with NaHCO$_3$ sat. (10 mL) and brine (10 mL). The organic layer was dried with Na$_2$SO$_4$, filtered and the solvent was evaporated under reduced pressure. The residue was loaded onto a silica gel flash column (SiO$_2$, hexane:ethyl acetate 9:1) to afford a yellow oil (0.014 g, 93%). ¹H-NMR (CDCl$_3$, 400 MHz): δ=6.93 (s, 1H), 4.19 (s, 1H, OH), 2.67 (t, J=8 Hz, 2H), 2.61 (m, 1H), 2.55 (m, 1H), 2.09 (s, 6H), 2.02 (s, 3H), 2.00 (m, 1H), 1.84 (m, 1H), 1.47 (s, 3H), 1.38 (m, 1H), 1.18 (m, 1H), 0.83 (t, J=8 Hz, 3H). MS (EI⁺): m/z (%): 319 (M⁺, 74), 164 (100), 121 (19). HRMS: m/z [M⁺] calcd. for C$_{18}$H$_{25}$NO$_4$: 319.1784, found: 319.1761.

Example 3

(±)-2,5,7,8-tetramethyl-2-[(E)-2-nitrooct-1-en-1-yl]chroman-6-ol (NATx8)

Steps 1-3 of Example 1 are repeated to prepare 4 (6-((tert-butoxycarbonyl)oxy)-2,5,7,8-tetramethylchroman-2-carbaldehyde).

Step 4. Preparation of tert-butyl (2,5,7,8-tetramethyl-2-[(E)-2-nitrooct-1-en-1-yl]chroman-6-yl) carbonate.

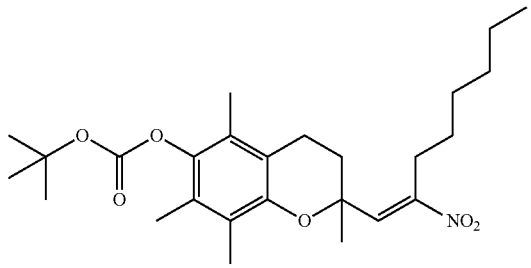 [SMILES: CCCCCC/C(=C\C1(C)CCc2c(C)c(OC(=O)OC(C)(C)C)c(C)c(C)c2O1)[N+](=O)[O-]]

A mixture of 1-nitroheptane (0.087 g, 0.60 mmol), aldehyde 4 (0.2 g, 0.6 mmol) and DBU (0.1 mL, 0.06 mmol) in acetonitrile (2 mL) was stirred at room temperature for 24 h. The solvent was removed under reduced pressure and the residue was loaded onto a silica gel column (SiO$_2$, Hexane:Ethyl acetate 85:15) to afford the nitrohydroxy product as a diasteromeric mixture (yellow oil, 0.214 g, 76%). MS (EI+): m/z (%): 479 (M+, 1.4), 379 (18), 234 (44), 205 (99), 57 (100). HRMS: m/z [M+] calcd. for C$_{26}$H$_{41}$NO$_7$: 479.2883, found: 479.2867.

To nitrohydroxy intermediate (0.2 g, 0.42 mmol) in dry DCM (5 mL) at 0° C., methanesulfonyl chloride (0.048 g, 0.42 mmol) and triethylamine (0.15 mL, 1.1 mmol) were added. After 2 h, complete formation of mesyl derivatives (as diasteromic mixture) was observed. Then DBU (0.16 g, 1.0 mmol) was added and reaction was stirred overnight. Water was added (15 mL) and compound was extracted with ethyl acetate (3×5 mL), dried with Na$_2$SO$_4$, filtered and solvent removed under reduced pressure. The residue was loaded onto a silica gel column (SiO$_2$, Hexane:Ethyl acetate 85:15) to afford the desire product as a yellow oil (0.09 g, 47%). ¹H-NMR (CDCl$_3$, 500 MHz): δ=6.91 (s, 1H), 2.69 (t, J=10.2 Hz, 2H), 2.60 (m, 1H), 2.54 (m, 1H), 2.07 (s, 3H), 2.01 (s, 3H), 1.99 (m, 1H), 1.95 (s, 3H), 1.83 (m, 1H), 1.48 (s, 9H), 1.47 (s, 3H), 1.35 (m, 1H), 1.19 (m, 6H), 1.06 (m, 1H), 0.81 (t, J=10.2 Hz, 3H). ¹³C-NMR (CDCl$_3$, 500 MHz):

δ 153.9, 152.1, 148.4, 141.7, 137.1, 128.2, 125.7, 122.6, 117.2, 82.85, 74.67, 32.97, 31.52, 29.39, 28.28, 27.71 (2C), 26.51, 22.56, 21.04, 14.04, 12.73, 12.08, 11.90. MS (EI+): m/z (%): 461 (M+, 5.50), 361 (72.10), 164.08 (30.36), 57.07 (100). HRMS: m/z [M+] calcd. for $C_{26}H_{39}NO_6$: 461.2777, found: 461.2763.

Step 5. Preparation of NATx8.

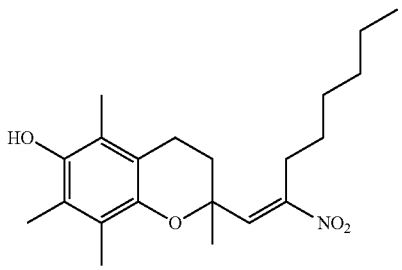 [SMILES: CCCCCC/C(=C\C1(C)CCc2c(C)c(O)c(C)c(C)c2O1)[N+](=O)[O-]]

Example 4

(±)-2,5,7,8-tetramethyl-2-[(E)-2-nitrotridec-1-en-1-yl]chroman-6-ol (NATx13)

Steps 1-3 of Example 1 are repeated to prepare 4 (6-((tert-butoxycarbonyl)oxy)-2,5,7,8-tetramethylchroman-2-carbaldehyde).

Step 4. Preparation of tert-butyl (2,5,7,8-tetramethyl-2-[(E)-2-nitrotridec-1-en-1-yl)chroman-6-yl) carbonate.

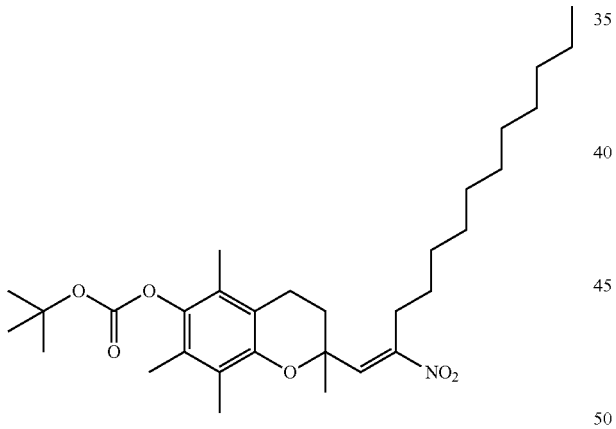

A mixture of 1-nitrododecane (0.13 g, 0.60 mmol), aldehyde 4 (0.2 g, 0.6 mmol) and DBU (0.1 mL, 0.06 mmol) in acetonitrile (2 mL) was stirred at room temperature for 24 h. The solvent was removed under reduced pressure and the residue was loaded onto a silica gel column (SiO$_2$, Hexane: Ethyl acetate 85:15) to afford the nitrohydroxy product as a diasteromeric mixture (yellow oil, 0.14 g, 42%). MS (EI+): m/z (%): 449 (6), 234 (27), 205 (61), 57 (100).

To nitrohydroxy intermediate(0.14 g, 0.26 mmol) in dry DCM (3 mL) at 0° C., methanesulfonyl chloride (0.030 g, 0.26 mmol) and triethylamine (0.068 mL, 0.7 mmol) were added. After 2 h, complete formation of mesyl derivatives (as diasteromic mixture) was observed. Then DBU (0.1 g, 0.65 mmol) was added and reaction was stirred overnight. Water was added (15 mL) and compound was extracted with ethyl acetate (3×5 mL), dried with Na$_2$SO$_4$, filtered and solvent removed under reduced pressure. The residue was loaded onto a silica gel column (SiO$_2$, Hexane:Ethyl acetate 85:15) to afford the desire product as a yellow oil (0.06 g, 44%). $^1$H-NMR (CDCl$_3$, 500 MHz): δ=6.91 (s, 1H), 2.69 (t, J=8.1 Hz, 2H), 2.60 (m, 1H), 2.55 (m, 1H), 2.07 (s, 3H), 2.01 (s, 3H), 1.97 (m, 1H), 1.96 (s, 3H), 1.83 (m, 1H), 1.47 (s, 9H), 1.46 (s, 3H), 1.31 (m, 1H), 1.18 (m, 16H), 1.08 (m, 1H), 0.82 (t, J=8.1 Hz, 3H). 13C-NMR (CDCl$_3$, 500 MHz): δ 154.0, 152.1, 148.4, 141.7, 137.1, 127.8, 125.7, 122.7, 117.2, 82.84, 74.64, 32.96, 31.92, 31.60, 29.72, 29.63, 29.62, 29.59, 29.55, 29.34, 28.32, 27.70, 26.50, 22.70, 21.03, 14.12, 12.73, 12.08, 11.89. MS (EI+): m/z (%): 531 (M+, 2.11), 431 (100), 164 (36), 57 (98). HRMS: m/z [M+] calcd. for $C_{31}H_{49}NO_6$: 531.3560, found: 531.3588.

Step 5. Preparation of NATx13.

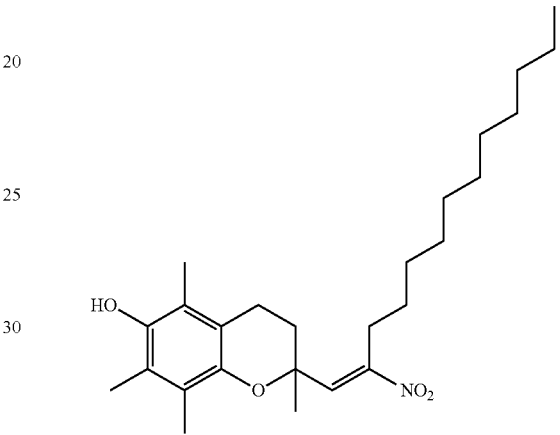

To a solution of tert-butyl (2,5,7,8-tetramethyl-2-(2-nitrotridec-1-en-1-yl)chroman-6-yl) carbonate (0.02 g, 0.038 mmol) in DCM (0.64 mL), TFA (0.064 mL, 0.83 mmol) was added and was agitated for 2 h at room temperature. Then, reaction mixture was washed with NaHCO$_3$ sat. (10 mL) and brine (10 mL). The organic layer was dried with Na$_2$SO$_4$, filtered and the solvent was evaporated under reduced pressure. The residue was loaded onto a silica gel flash column (SiO$_2$, hexane:ethyl acetate 85:15) to afford a yellow oil (0.01 g, 63%). $^1$H-NMR (CDCl$_3$, 400 MHz): δ=6.98 (s, 1H), 4.23 (s, 1H), 2.75 (m, 2H), 2.68 (m, 1H), 2.63 (m, 1H), 2.16 (s, 3H), 2.15 (s, 3H), 2.10 (s, 3H), 2.06 (m, 1H), 1.91 (m, 1H), 1.54 (s, 3H), 1.30 (m, 17H), 1.14 (m, 1H), 0.90 (t, J=8.0 Hz, 3H). MS (EI+): m/z (%): 431 (M+, 100), 164 (77), 57 (20). HRMS: m/z [M+] calcd. for $C_{26}H_{41}NO_4$: 431.3036, found: 431.3030.

Example 5

(±)-2,5,7,8-tetramethyl-2-[(E)-5-nitrohex-4-en-1-yl]chroman-6-ol

Step 1. Preparation of tert-butyl 2-(4-hydroxybut-1-enyl)-2,5,7,8-tetramethylchroman-6-yl carbonate.

A suspension of the phosphonium salt (1 mmol) in dry THF (10 mL) at room temperature under argon was treated dropwise with a THF solution of LiHMDS (0.9 M in THF, 2.5 mmol) via a syringe. The red ylide was stirred for 1 h under argon, and then a solution of 6-((tert-butoxycarbonyl)oxy)-2,5,7,8-tetramethylchroman-2-carbaldehyde (1 mmol) in THF was added dropwise. The color changed from red to pale yellow. The resulting suspension was stirred for an additional 3 h until aldehyde could not be detected by TLC. The reaction was quenched with saturated NH₄Cl (25 mL) and water (25 mL) and then extracted with ethyl acetate. After solvent removal, trituration with cold hexane removed triphenylphosphine oxide. Concentration of the hexane solution and purification by column chromatography on silica gel rendered the desired product.

Step 2. Preparation of tert-butyl 2-(4-hydroxybutyl)-2,5,7,8-tetramethylchroman-6-yl carbonate.

To a solution of tert-butyl 2-(4-hydroxybut-1-enyl)-2,5,7,8-tetramethylchroman-6-yl carbonate (1 mmol) in ethyl acetate (20 mL) was added 140 mg of 10% Pd/C, and the reaction mixture was attached to a hydrogen balloon for 18 h. Filtering and evaporation afforded desired compound. The product was directly used for next step without any purification.

Step 3. Preparation of tert-butyl 2-(4-oxobutyl)-2,5,7,8-tetramethylchroman-6-yl carbonate.

To a solution of tert-butyl 2-(4-hydroxybutyl)-2,5,7,8-tetramethylchroman-6-yl carbonate (1.5 mmol) and TEMPO (0.32 mmol) in acetone, (diacetoxyiodo)benzene (2.0 mmol) was added. After 20 h of stirring at room temperature the reaction mixture was washed with water and extracted with diethyl ether. The organic layers were dried with $Na_2SO_4$, filtered and the solvent was evaporated under reduced pressure. The residue was loaded onto a silica gen flash column and eluted with hexane:ethyl acetate to afford the desire product.

Step 4. Preparation of tert-butyl 2-(5-nitrohex-4-en-1-yl) 2,5,7,8-tetramethyl-chroman-6-yl carbonate.

Aldehyde tert-butyl 2-(4-oxobutyl)-2,5,7,8-tetramethyl-chroman-6-yl carbonate (1 mmol) was added in a mixture of nitroethane (3 mL) and equivalent amount of $CH_3COONH_4$. The mixture was stirred at 100° C. for 2 h. The solvent was then evaporated and water and diethyl ether were added. The organic layer was washed with H2O, HCl 1N, and saturated aqueous NaCl, dried, and the solvent was evaporated. The crude residue was purified by column chromatography affording the desired nitrovinyl compound.

Step 5. Preparation of (±)-2,5,7,8-tetramethyl-2-[(E)-5-nitrohex-4-en-1-yl]chroman-6-ol.

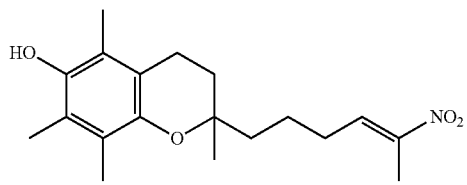 [SMILES: C/C(=C\CCCC1(C)CCc2c(C)c(O)c(C)c(C)c2O1)[N+](=O)[O-]]

To a solution of tert-butyl 2-(5-nitrohex-4-en-1-yl) 2,5,7,8-tetramethyl-chroman-6-yl carbonate (1 mmol) in DCM, TFA (22 mmol) was added and the reaction was stirred for 2 h at room temperature. Then, the reaction mixture was washed with $NaHCO_3$ saturated solution and brine. The organic layers were dried with $Na_2SO_4$, filtered and solvent evaporated under reduced pressure. The residue was loaded onto a silica gel flash column and eluted with hexane:ethyl acetate to afford final product.

Biologic Activity

The following methods described are used in order to demonstrate biological activity and therapeutic use, and should not to be construed in any way as limiting the scope of the invention.

In Vitro Activity

As shown in FIG. 1A, 130 μM of 2,5,7,8-tetramethyl-2-[(E)-2-nitrovinyl]chroman-6-ol (NATx0) was incubated with 1 mM of β-mercaptoethanol (Sigma) in 100 mM pH7 phosphate buffer. UV-visible spectra was acquired by a Varian Cary 50 Bio. Scans were taken every min up to 15 min.

Figure 1B:
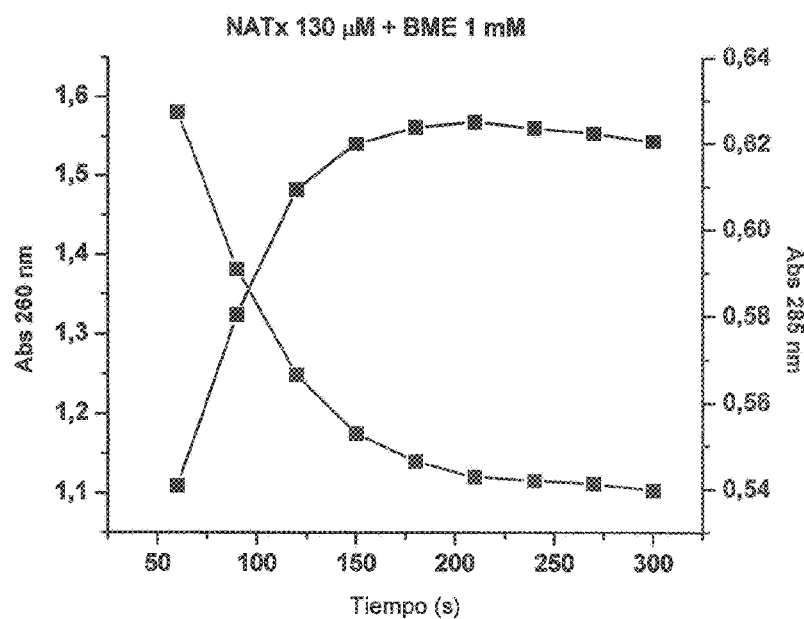

The reaction between NATx0 and β-mercaptoethanol (BME) showed decrease in the absorbance at the maximums at 285 nm and showed increase at the 260 nm wavelength as shown in FIG. 1B. The increase at 260 nm demonstrates adduct formation between NATx0 and BME, and the decrease of the maximums at 285 nm exhibits NATx0 consumption.

Figure 2:
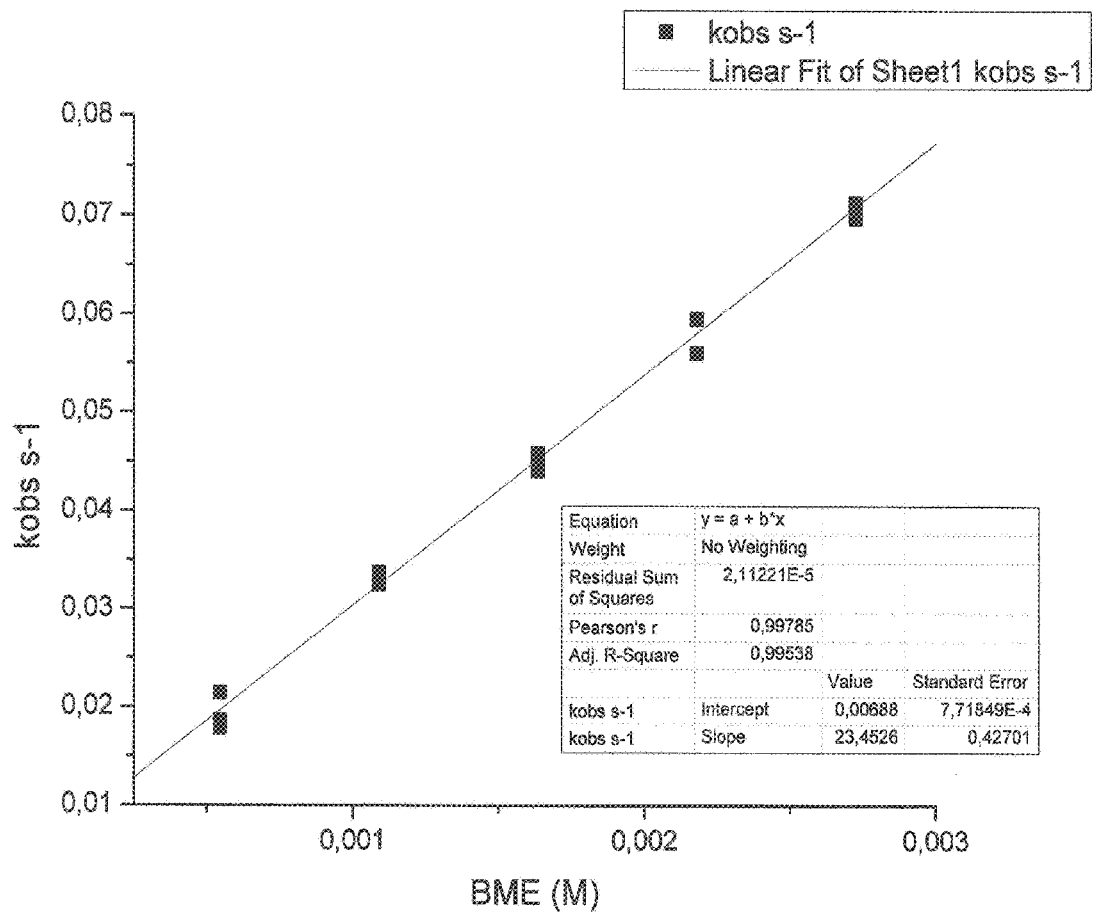
FIG. 2 demonstrates that the adduct formation follows a second order rate constant.

In FIG. 2, it is shown that the reaction between NATx0 and BME was determined to be a second order rate constant. Stopped-flow kinetic measurements were performed using a Rx 2000 stopped flow analyzer (Applied Photophysics). Mixtures of 150 μL NATx0 (25 μM) and solutions of BME at 0.54 mM, 1.09 mM, 1.64 mM, 2.18 mM, and 2.73 mM concentrations.

The reaction was monitored by following the absorbance at 260 nm and plots were fitted to a simple exponential decay function using Originlab software (version 8.0. The observed pseudo first order constant at each concentration of BME was extracted from the equation and plotted against the concentration of BME. The second rate constant of the reaction is derived from the slope of the curve and was 23.45 $M^{-1}s^{-1}$. All experiments were carried out at 25° C. by triplicate.

Figure 3:
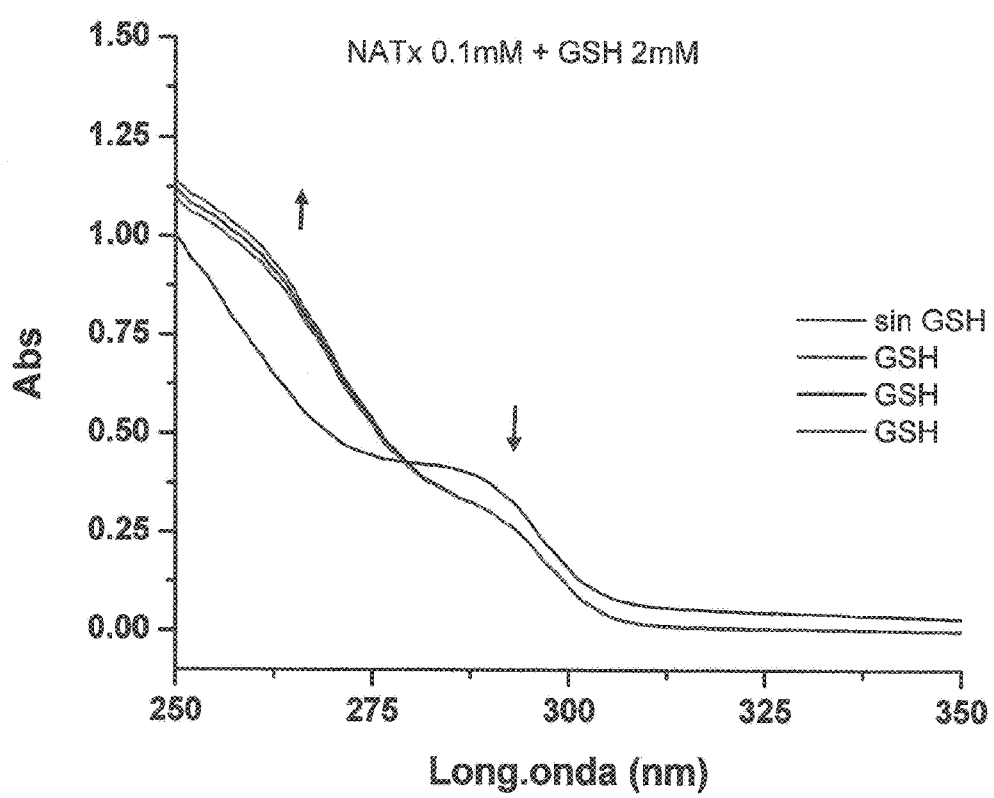
FIG. 3 further confirms adduct formation between sulfur moieties and the nitro vinyl β-carbon via Michael addition, but demonstrated with glutathione.

In FIG. 3, 130 μM NATx0 was incubated with 2 mM Glutathione (Sigma) in 100 mM pH 7 phosphate buffer. UV-visible spectra was acquired by a Varian Cary 50 Bio. Scans were taken every min up to 15 min. The reaction between NATx0 and β-mercaptoethanol (BME) showed decrease in the absorbance at the maximums at 285 nm and showed increase at the 260 nm wavelength. The increase at 260 nm demonstrates adduct formation between NATx0 and BME, and the decrease of the maximums at 285 nm exhibits NATx0 consumption.

The reaction between NATx0 and glutathione (GSH) showed decrease in the absorbance at the maximums at 285 nm and showed increase at the 260 nm wavelength. The increase at 260 nm demonstrates adduct formation between NATx0 and BME, and the decrease of the maximums at 285 nm exhibits NATx0 consumption. The results shown in FIG. 2 further demonstrates that compounds within the scope of the present invention form adducts with proteins that modulate cell signaling cascades through Michael addition between the electrophilic β-carbon of the nitroalkene moiety and the nucleophilic thiol contain residues.

Figure 4:
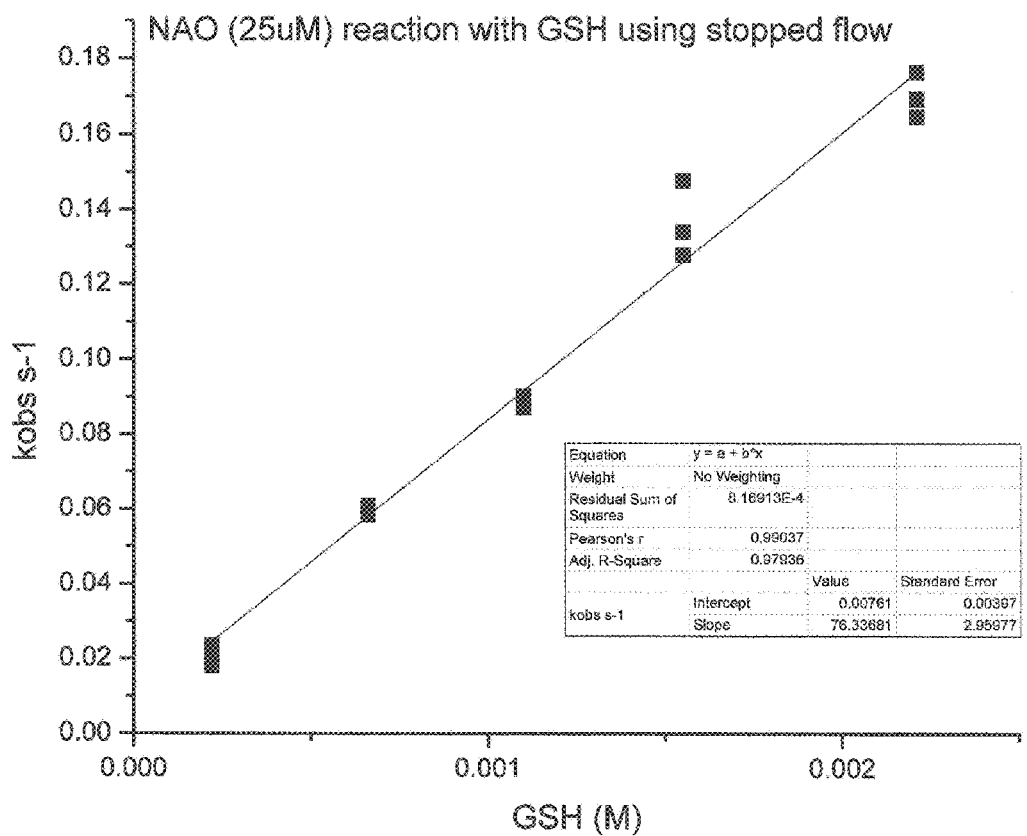
FIG. 4 demonstrates that the adduct formation with the sulfur moiety in glutathione followed a second order rate reaction.

FIG. 4 illustrates a second order rate constant of the reaction between NATx0 and GSH. Stopped-flow kinetic measurements were performed using a Rx 2000 stopped flow analyzer (Applied Photophysics). Mixtures of 150 μL NATx0 (25 μM) and solutions of BME at 0.54 mM, 1.09 mM, 1.64 mM, 2.18 mM, and 2.73 mM concentrations.

The reaction was monitored by following the absorbance at 260 nm and plots were fitted to a simple exponential decay function using Originlab software (version 8.0. The observed pseudo first order constant at each concentration of BME was extracted from the equation and plotted against the concentration of BME. The second rate constant of the reaction is derived from the slope of the curve and was 23.45 $M^{-1}s^{-1}$. All experiments were carried out at 25° C. by triplicate.

Figure 5:
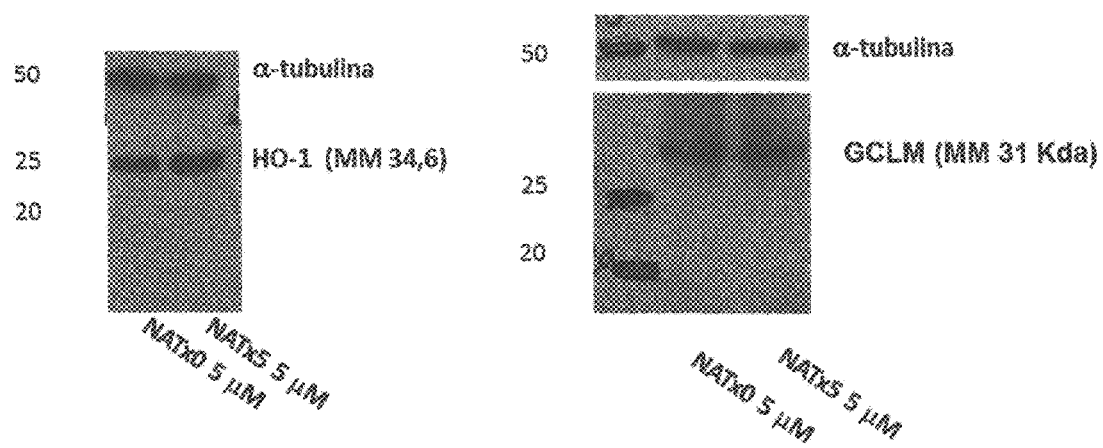
FIG. 5 provides Western Blot analysis to illustrate HO-1 and GCLM protein expression by macrophage cell lines after exposure to NATx0 or NATx5.

As shown in FIG. 5, Western Blot analysis was performed to investigate HO-1 and GCLM protein expression after exposure to the NATx compounds including NATx0 and 2,5,7,8-tetramethyl-2-[(E)-2-nitropent-1-enyl]chroman-6-ol (NATx5). Raw 264.7 cells, a murine macrophage cell line catalog no. TIB-71TM (ATCC, Manassas, Va.), were treated with NATx0 or NATx5 (5 µM) for 18 hours. Cells were lysed, and total protein concentration was measured with Pierce BCA assay (Thermo Fisher Scientific, Rockford, Ill.). For electrophoresis, 30 µg of protein was used in each line. The proteins were electrophoresed on a Tris/glycine SDS-polyacrylamide gradient gel (10-15%) and transferred to nitrocellulose membrane. The primary antibodies used for detection was rabbit polyclonal anti-HO-1 or anti-GCLM (Abcam, Cambridge, Mass.). Blots were visualized using horseradish peroxidase-conjugated secondary antibodies and ECL Plus detection system (GE Healthcare, Little Chalfont, UK). Blots were detected with a scanner. Protein expression was quantified with ImageQuant TL7.0 software (GE Healthcare, Little Chalfont, UK). The results shown demonstrate that Both NATx compounds induced the expression of HO-1 and GCLM, under the control of the Nrf2/Keap1 system.

Figure 6A:
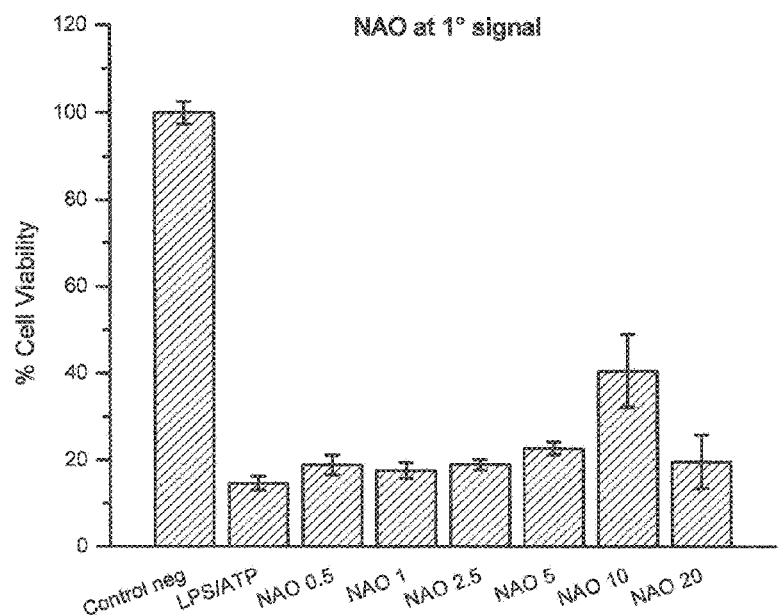
FIGS. 6A and 6B demonstrates that NATx0 did not induce an increase in cell mortality nor did it protect cells when cells were activated with LPS.
Figure 6B:
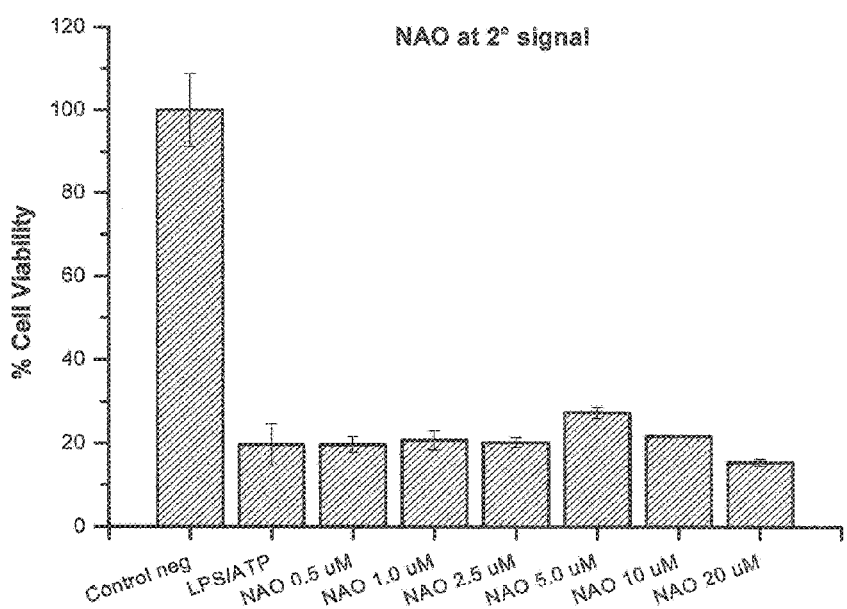

FIGS. 6A and 6B illustrate the effect of NATx0 on cell viability and NLRP3 inflammasome activation. THP-1 cells were differentiated into macrophages (PMA 200 nM, 48 hours). As shown in FIG. 6A, the cells were then stimulated with LPS (first signal; 250 ng/mL, 3 hours). Subsequently, as shown in FIG. 6B, the cells were stimulated with ATP (second signal; 5 mM, 45 minutes). The cells were treated with NATx0 at 0.5 µM, 1.0 µM, 2.5 µM, 5.0 µM, 10 µM and 20 µM concentrations together with the first signal or the second signal. Cell viability was measured by MTT assay. Supernatant was stored.

Figure 7A:
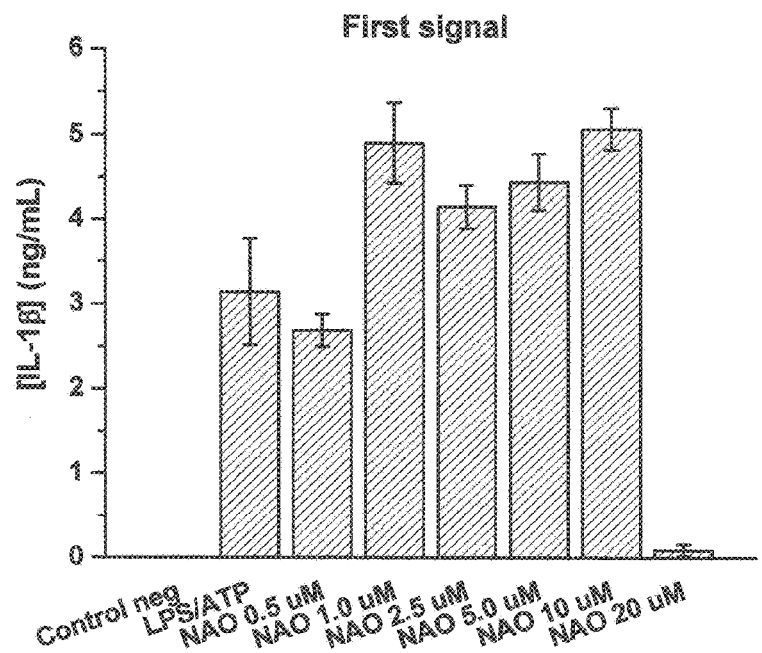
FIGS. 7A and 7B illustrates inhibition of NLRP3 inflammasome activation at 20 μM of NATx0 when applied with the first signal to activate the inflammasome (meaning NFkB related mechanisms) but already at 5 μM when applied together with the second inflammasome-activating signal (meaning post-translational modification mechanism at the supramolecular inflammasome complex).
Figure 7B:
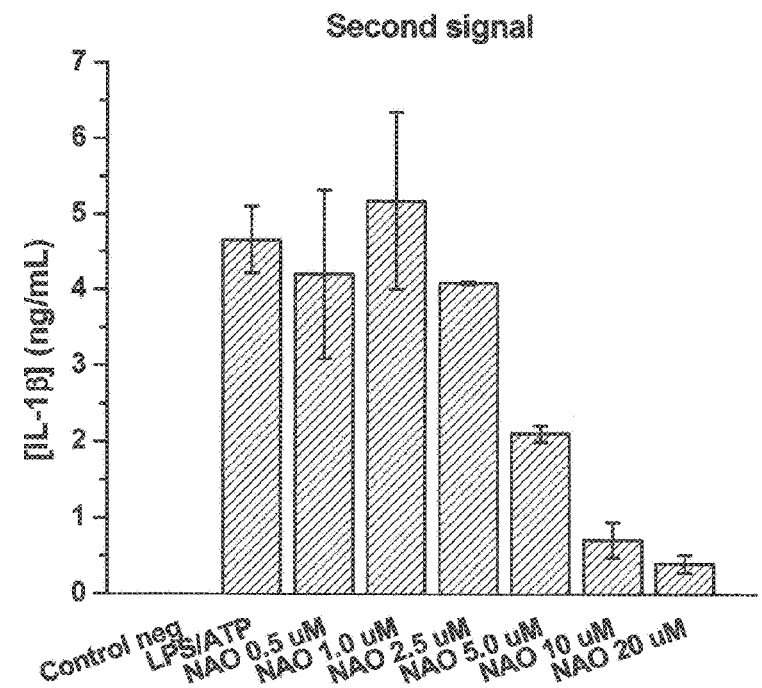

In FIGS. 7A and 7B, supernatant stored from the previously described experiment were measured for IL-1β by ELISA.

FIGS. 6 and 7 demonstrate that NATx0 does not induce an increase in cell mortality induced by the activation of the cells by LPS or ATP, nor did it protect the cells. On the other hand, NATx0 inhibited inflammasome activation in dose dependent manner when applied together with the second signal. At the first signal, we only observed a full inhibition of the inflammasome at 20 µM.

Figure 8:
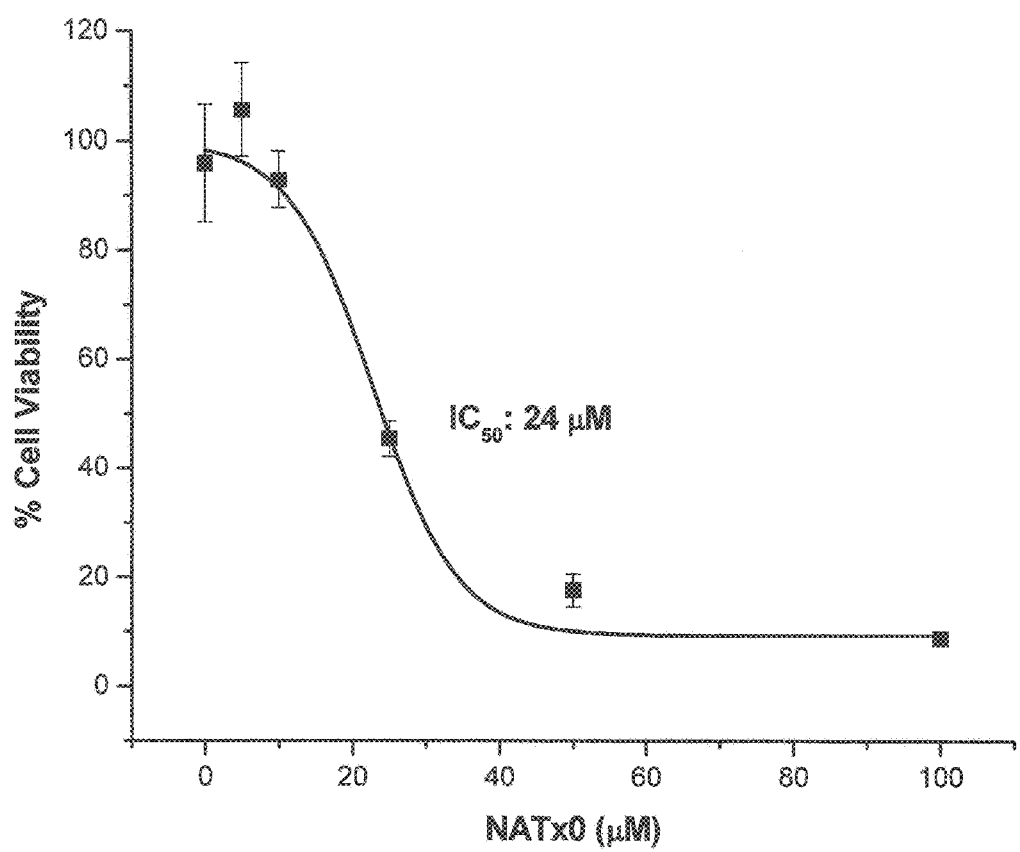
FIG. 8 presents cytotoxicity data of NATx0 in RAW 264.7 murine cells.

FIG. 8 NATx0 cell cytotoxicity was evaluated in RAW 264.7 cells at 1, 5, 10, 50 and 100 µM in DMSO. Cells were treated for 24 h with NATx0 and then MTT assay was performed. The absorbance at 570 nm was measured for each condition by triplicate. The % cell liability was calculated using control group (DMSO, without treatment). The half maximal inhibitory concentration ($IC_{50}$) was calculated after % cell viability was plotted against the concentration of NATx0 and fitted to an exponential function using Origin-Lab software (version 8.0). The $IC_{50}$ for NATx0 in RAW 264.7 cells was calculated to be 24 µM.

Figure 9:
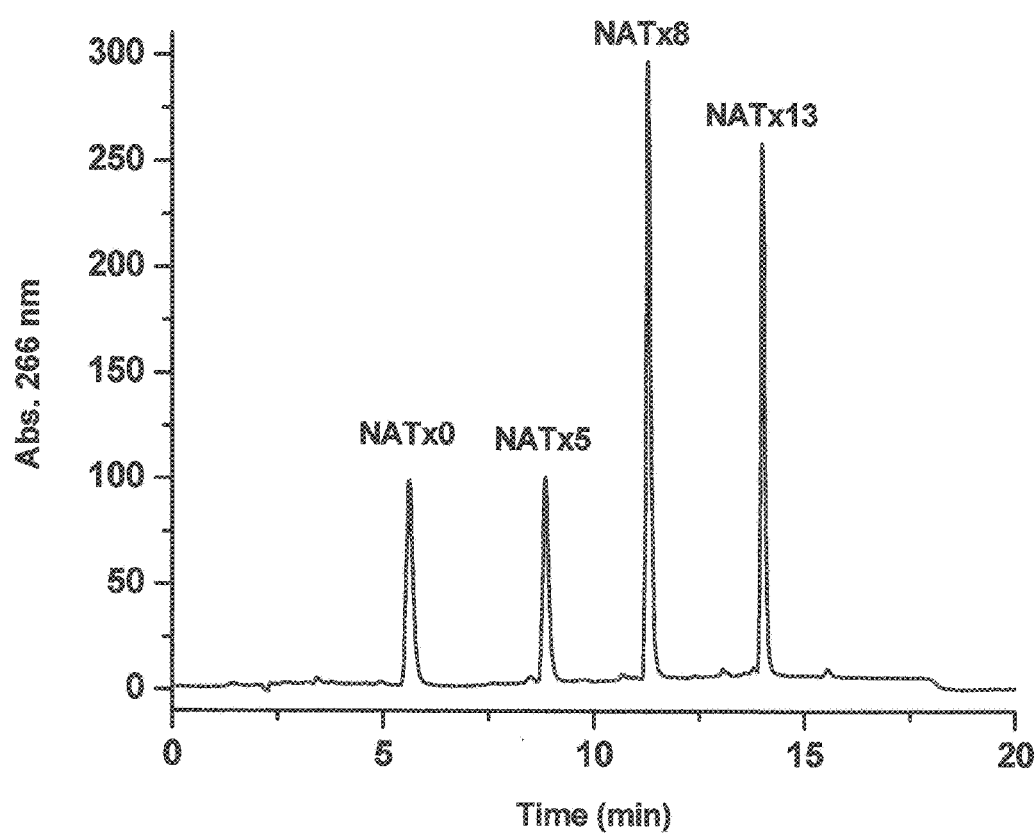
FIG. 9 demonstrates control over the lipophilicity of the compounds, illustrating the scope of the molecules to range from water-soluble to fat-soluble as studied by RP-HPLC.

FIG. 9 illustrates control of the hydrophilicity of embodiments of trolox derivatives described herein. Reverse phase chromatography was performed on a C30 column at 1.5ml/min. The solvents used were A: $H_2O$ and methanol (MeOH). The gradient used was 75% MeOH from 0 to 3 minutes and 100% MeOH from 3 to 10 minutes. Compounds were detected at 266 nm with a 10 nmol injection volume.

Figure 10:
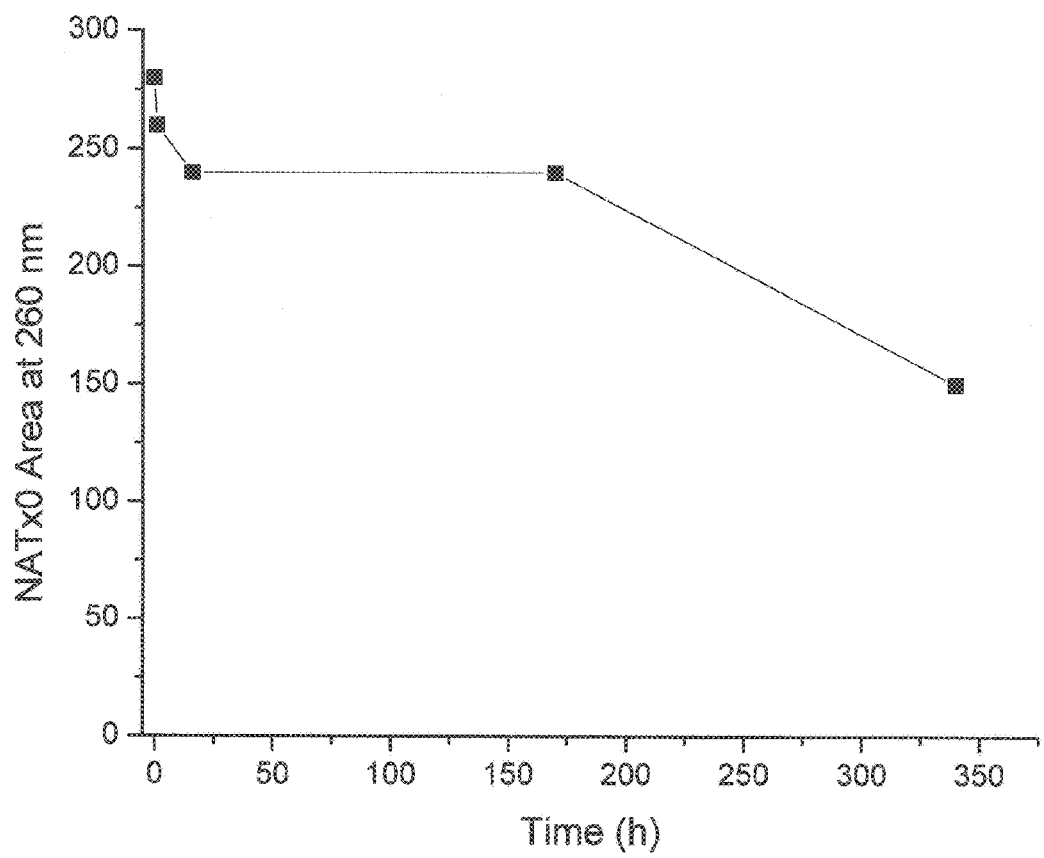
FIG. 10 illustrates the stability of NATx0 in polyethylene glycol 300-400 at 37° C.

FIG. 10 presents the incubation of NATx0 incubated in PEG 300 to PEG 400 at 37° C. for two weeks. At each time point, an aliquot was extracted with methanol and analyzed by reverse phase chromatography as before. After two weeks in 37° C. in PEG, 50% of the initial concentration of NATx0 was recovered.

Figure 11:
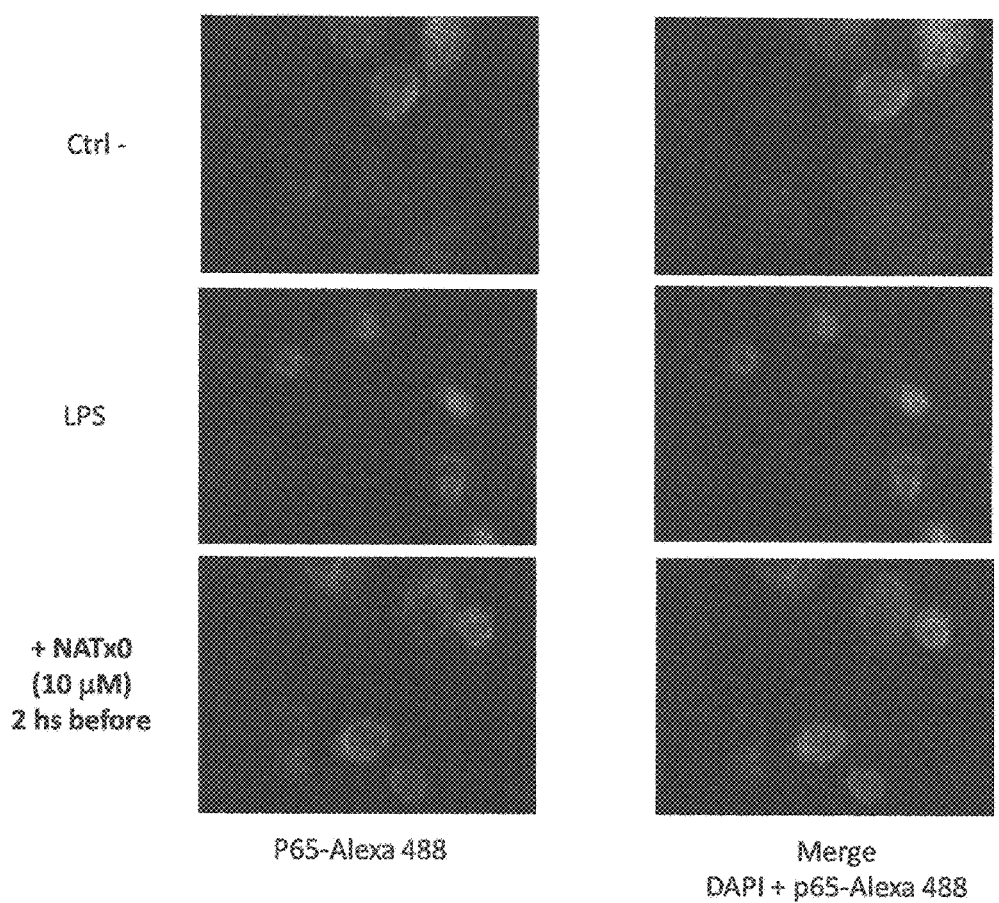
FIG. 11 illustrates immunofluorescence and epifluorescence microscopy analysis showing that NATx0 inhibits nuclear translocation of NF-κB in THP-1 macrophages.

Nuclear factor kappa B (NF-κB) represents a family of pro-inflammatory transcription factors, present in all eukaryotic cells, which regulate inducible expression of wide ranging genes involved in immune responses and cell-cycle regulation. Activation of NF-κB is accompanied by nuclear translocation of NF-κB. Accordingly, FIG. 11 illustrates the lack of nuclear translocation of NF-κB in the presence of nitroalkene trolox derivatives to further demonstrate anti-inflammatory effects. Specifically, FIG. 11 illustrates immunofluorescence and epifluorescence microscopy analysis showing the effect of NATx0 on LPS-induced NF-κB/p65 subcellular localization in THP-1 macrophages. Cells treated with NATx0 (10 uM, 2 hs before) and then activated with LPS (1 ug/mL) show no change from the negative control (Ctrl-) cells which were not treated with LPS. However, the cells that were not treated with NATx0 and activated with LPS showed nuclear translocation of NF-κB p65 dimers tagged with Alexa 488 antibodies.

In Vivo Activity

Figure 12:
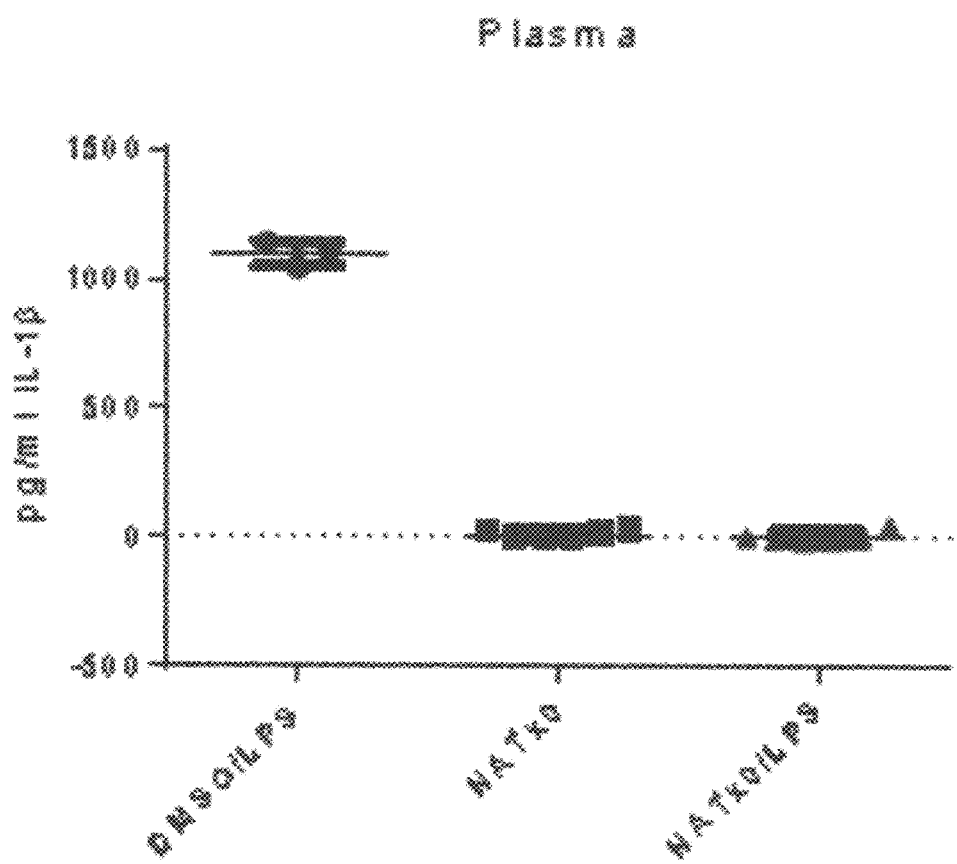
FIG. 12 demonstrates the potent in vivo anti-inflammatory effects of NATx0 in C57BL/6 mice.

In vivo testing was carried out in C57BL/6 mice. The mice were injected intraperitoneally ("i.p.") with 20 mg/kg NATx0 or a control (DMSO) 1 hour before i.p. injection of 10 mg/kg LPS *Escherichia coli* 055:B5 (Sigma-Aldrich). After 2 hours the mice were killed, and serum levels of IL-1β were measured by ELISA to determine inflammatory response. FIG. 12 illustrates that the inflammatory response did not increase in mice injected with NATx0, whereas the mice injected with the control showed dramatic increases indicating NATx0 is a potent anti-inflammatory agent.

Non-Patent Citations

1. Kansanen, E., Jyrkkanen, H. K., Volger, O. L., Leinonen, H., Kivela, A. M., Hakkinen, S. K., Woodcock, S. R., Schopfer, F. J., Horrevoets, A. J., Yla-Herttuala, S., Freeman, B. A., and Levonen, A. L. (2009) Nrf2-dependent and -independent responses to nitro-fatty acids in human endothelial cells: identification of heat shock response as the major pathway activated by nitro-oleic acid, J Biol Chem 284, 33233-33241.

2. Batthyany C, Schopfer F J, Baker P R, Duran R, Baker L M, Huang Y, Cervenansky C, Branchaud B P, Freeman B A (2006) Reversible post-translational modification of proteins by nitrated fatty acids in vivo. J Biol Chem 281: 20450-20463.

3. Motohashi, H., and Yamamoto, M. (2004) Nrf2-Keap1 defines a physiologically important stress response mechanism, Trends Mol Med 10, 549-557.

4. Khoo, N. K., and Freeman, B. A. (2010) Electrophilic nitro-fatty acids: anti-inflammatory mediators in the vascular compartment, Current opinion in pharmacology 10, 179-184.

5. Holtzclaw, W. D., Dinkova-Kostova, A. T., and Talalay, P. (2004) Protection against electrophile and oxidative stress by induction of phase 2 genes: the quest for the elusive sensor that responds to inducers, Adv Enzyme Regul 44, 335-367.

6. Levonen, A. L., Inkala, M., Heikura, T., Jauhiainen, S., Jyrkkanen, H. K., Kansanen, E., Maatta, K., Romppanen, E., Turunen, P., Rutanen, J., and Yla-Herttuala, S. (2007) Nrf2 gene transfer induces antioxidant enzymes and suppresses smooth muscle cell growth in vitro and reduces oxidative stress in rabbit aorta in vivo, Arterioscler Thromb Vasc Biol 27, 741-747.

7. Talalay, P., Dinkova-Kostova, A. T., and Holtzclaw, W. D. (2003) Importance of phase 2 gene regulation in protection against electrophile and reactive oxygen toxicity and carcinogenesis, Adv Enzyme Regul 43, 121-134.

8. Wakabayashi, N., Dinkova-Kostova, A. T., Holtzclaw, W. D., Kang, M. I., Kobayashi, A., Yamamoto, M., Kensler, T. W., and Talalay, P. (2004) Protection against electrophile and oxidant stress by induction of the phase 2 response: fate of cysteines of the Keap1 sensor modified by inducers, Proc Natl Acad Sci USA 101, 2040-2045.

9. Kansanen, E., Bonacci, G., Schopfer, F. J., Kuosmanen, S. M., Tong, K. I., Leinonen, H., Woodcock, S. R., Yamamoto, M., Carlberg, C., Yla-Herttuala, S., Freeman, B. A., and Levonen, A. L. (2011) Electrophilic nitro-fatty acids activate NRF2 by a KEAP1 cysteine 151-independent mechanism, J Biol Chem 286, 14019-14027.

10. Abraham, N. G., and Kappas, A. (2005) Heme oxygenase and the cardiovascular-renal system, Free radical biology & medicine 39, 1-25.

11. Baker, P. R., Schopfer, F. J., O'Donnell, V. B., and Freeman, B. A. (2009) Convergence of nitric oxide and lipid signaling: anti-inflammatory nitro-fatty acids, Free radical biology & medicine 46, 989-1003.

12. Cock T A, Houten S M, Auwerx J (2004) Peroxisome proliferator-activated receptor-gamma: too much of a good thing causes harm. EMBO Rep 5: 142-147.

13. Baker P R, Schopfer F J, O'Donnell V B, Freeman B A (2009) Convergence of nitric oxide and lipid signaling: anti-inflammatory nitro-fatty acids. Free Radic Biol Med 46: 989-1003.

14. Yu K, Bayona W, Kallen C B, Harding H P, Ravera C P, McMahon G, Brown M, Lazar M A (1995) Differential activation of peroxisome proliferator-activated receptors by eicosanoids. J Biol Chem 270: 23975-23983.

15. Shiraki T, Kamiya N, Shiki S, Kodama T S, Kakizuka A, Jingami H (2005) Alpha,beta-unsaturated ketone is a core moiety of natural ligands for covalent binding to peroxisome proliferator-activated receptor gamma. J Biol Chem 280: 14145-14153.

16. Elbrecht A, Chen Y, Adams A, Berger J, Griffin P, Klatt T, Zhang B, Menke J, Zhou G, Smith R G, Moller D E (1999) L-764406 is a partial agonist of human peroxisome proliferator-activated receptor gamma. The role of Cys313 in ligand binding. J Biol Chem 274: 7913-7922.

17. Khoo N K, Freeman B A (2010) Electrophilic nitro-fatty acids: anti-inflammatory mediators in the vascular compartment. Curr Opin Pharmacol 10: 179-184.

18. Li Y, Zhang J, Schopfer F J, Martynowski D, Garcia-Barrio M T, Kovach A, Suino-Powell K, Baker P R, Freeman B A, Chen Y E, Xu H E (2008) Molecular recognition of nitrated fatty acids by PPAR gamma. Nat Struct Mol Biol 15: 865-867.

19. Schopfer F J, Cole M P, Groeger A L, Chen C S, Khoo N K, Woodcock S R, Golin-Bisello F, Motanya U N, Li Y, Zhang J, Garcia-Barrio M T, Rudolph T K, Rudolph V, Bonacci G, Baker P R, Xu H E, Batthyany C I, Chen Y E, Hallis T M, Freeman B A (2010) Covalent peroxisome proliferator-activated receptor gamma adduction by nitrofatty acids: selective ligand activity and anti-diabetic signaling actions. J Biol Chem 285: 12321-12333.

20. Bouhlel M A, Derudas B, Rigamonti E, Dievart R, Brozek J, Haulon S, Zawadzki C, Jude B, Torpier G, Marx N, Staels B, Chinetti-Gbaguidi G (2007) PPARgamma activation primes human monocytes into alternative M2 macrophages with anti-inflammatory properties. Cell Metab 6: 137-143.

21. Rudolph V, Schopfer F J, Khoo N K, Rudolph T K, Cole M P, Woodcock S R, Bonacci G, Groeger A L, Golin-Bisello F, Chen C S, Baker P R, Freeman B A (2009) Nitro-fatty acid metabolome: saturation, desaturation, beta-oxidation, and protein adduction. J Biol Chem 284: 1461-1473.

22. Rudolph, V., Schopfer, F. J., Khoo, N. K., Rudolph, T. K., Cole, M. P., Woodcock, S. R., Bonacci, G., Groeger, A. L., Golin-Bisello, F., Chen, C. S., Baker, P. R., and Freeman, B. A. (2009) Nitro-fatty acid metabolome: saturation, desaturation, beta-oxidation, and protein adduction. *J Biol Chem* 284, 1461-73.

What is claimed is:

1. A compound of Formula I:

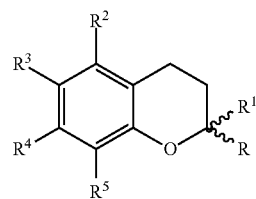

or a pharmaceutically-acceptable salt thereof, wherein R is a $C_1$-$C_{15}$ nitroalkenyl of formula Ia;

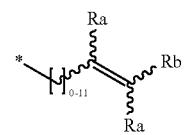

wherein one Ra is H and the other Ra is $NO_2$;
Rb is H or $C_1$-$C_{11}$ alkyl,
$R^1$, $R^2$, $R^4$, and $R^5$ are independently a —H or —$CH_3$; and
$R^3$ is selected from the group consisting of —H, —OH, —OBOC, —$OCH_3$, —OBn, —SH, —$NO_2$, —$NH_2$, —CN, a carbonyl, a sulfonate, an amidino.

2. The compound of claim 1, wherein $R^3$ is selected from the group consisting of —H, a —OH, —OBOC, —$OCH_3$, and —OBn.

3. The compound of claim 1, wherein $R^1$, $R^2$, $R^4$, and $R^5$ are each —$CH_3$.

4. The compound of claim 1, wherein R is a nitrovinyl.

5. The compound of claim 1, wherein $R^3$ is —OH.

6. The compound of claim 1 selected from the group consisting of:

2,5,7,8-tetramethyl-2-(2-nitrovinyl)chroman-6-ol,
2,5,7,8-tetramethyl-2-(2-nitropentenyl)chroman-6-ol,
2,5,7,8-tetramethyl-2-(2-nitro-2-pentenyl)chroman-6-ol,
2,5,7,8-tetramethyl-2-(3-nitro-2-pentenyl)chroman-6-ol,
2,5,7,8-tetramethyl-2-(3-nitro-3-pentenyl)chroman-6-ol,
2,5,7,8-tetramethyl-2-(4-nitro-3-pentenyl)chroman-6-ol,
2,5,7,8-tetramethyl-2-(4-nitro-4-pentenyl)chroman-6-ol,
2,5,7,8-tetramethyl-2-(5-nitro-4-pentenyl)chroman-6-ol,
2,5,7,8-tetramethyl-2-(2-nitrooctenyl)chroman-6-ol,
2,5,7,8-tetramethyl-2-(2-nitro-2-octenyl)chroman-6-ol,
2,5,7,8-tetramethyl-2-(3-nitro-2-octenyl)chroman-6-ol,
2,5,7,8-tetramethyl-2-(3-nitro-3-octenyl)chroman-6-ol,
2,5,7,8-tetramethyl-2-(4-nitro-3-octenyl)chroman-6-ol,
2,5,7,8-tetramethyl-2-(4-nitro-4-octenyl)chroman-6-ol,
2,5,7,8-tetramethyl-2-(5-nitro-4-octenyl)chroman-6-ol,
2,5,7,8-tetramethyl-2-(5-nitro-5-octenyl)chroman-6-ol,
2,5,7,8-tetramethyl-2-(6-nitro-5-octenyl)chroman-6-ol, 2,5,7,8-tetramethyl-2-(6-nitro-6-octenyl)chroman-6-ol,
2,5,7,8-tetramethyl-2-(7-nitro-6-octenyl)chroman-6-ol,
2,5,7,8-tetramethyl-2-(7-nitro-7-octenyl)chroman-6-ol,
2,5,7,8-tetramethyl-2-(8-nitro-7-octenyl)chroman-6-ol,
2,5,7,8-tetramethyl-2-(2-nitrotridecenyl)chroman-6-ol,
2,5,7,8-tetramethyl-2-(2-nitro-2-tridecenyl)chroman-6-ol,
2,5,7,8-tetramethyl-2-(3-nitro-2-tridecenyl)chroman-6-ol,
2,5,7,8-tetramethyl-2-(3-nitro-3-tridecenyl)chroman-6-ol,
2,5,7,8-tetramethyl-2-(4-nitro-3-tridecenyl)chroman-6-ol,
2,5,7,8-tetramethyl-2-(4-nitro-4-tridecenyl)chroman-6-ol,
2,5,7,8-tetramethyl-2-(5-nitro-4-tridecenyl)chroman-6-ol,
2,5,7,8-tetramethyl-2-(5-nitro-5-tridecenyl)chroman-6-ol,
2,5,7,8-tetramethyl-2-(6-nitro-5-tridecenyl)chroman-6-ol,
2,5,7,8-tetramethyl-2-(6-nitro-6-tridecenyl)chroman-6-ol,
2,5,7,8-tetramethyl-2-(7-nitro-6-tridecenyl)chroman-6-ol,
2,5,7,8-tetramethyl-2-(7-nitro-7-tridecenyl)chroman-6-ol,
2,5,7,8-tetramethyl-2-(8-nitro-7-tridecenyl)chroman-6-ol,
2,5,7,8-tetramethyl-2-(8-nitro-8-tridecenyl)chroman-6-ol,
2,5,7,8-tetramethyl-2-(9-nitro-8-tridecenyl)chroman-6-ol,
2,5,7,8-tetramethyl-2-(9-nitro-9-tridecenyl)chroman-6-ol,
2,5,7,8-tetramethyl-2-(10-nitro-9-tridecenyl)chroman-6-ol,
2,5,7,8-tetramethyl-2-(10-nitro-10-tridecenyl)chroman-6-ol,
2,5,7,8-tetramethyl-2-(11-nitro-10-tridecenyl)chroman-6-ol,
2,5,7,8-tetramethyl-2-(11-nitro-11-tridecenyl)chroman-6-ol,
2,5,7,8-tetramethyl-2-(12-nitro-11-tridecenyl)chroman-6-ol,
2,5,7,8-tetramethyl-2-(12-nitro-12-tridecenyl)chroman-6-ol,
2,5,7,8-tetramethyl-2-(13-nitro-12-tridecenyl)chroman-6-ol,
or a physiologically acceptable salt thereof.

7. 2,5,7,8-tetramethyl-2-(2-nitrovinyl)chroman-6-ol or a physiologically acceptable salt thereof.

8. The compound of claim 7 that is (2S)-2,5,7,8-tetramethyl-2-[(E)-2-nitrovinyl]chroman-6-ol or a physiologically acceptable salt thereof.

9. The compound of claim 1, wherein R is a 2-nitrovinyl and the absolute configuration of the chiral carbon adjacent the oxygen atom on the chromanol ring structure is (S).

10. The compound of claim 1, wherein R is a 2-nitroalkenyl and the absolute configuration of the chiral carbon adjacent the oxygen atom on the chromanol ring structure is (S).

11. A pharmaceutical composition comprising the compound of claim 1 and a carrier.

12. A pharmaceutical composition comprising the compound of claim 6 and a carrier.

13. A pharmaceutical composition comprising the compound of claim 7 and a carrier.

14. A pharmaceutical composition comprising the compound of claim 8 and a carrier.

* * * * *